US012239696B2

(12) United States Patent
Marconi et al.

(10) Patent No.: US 12,239,696 B2
(45) **Date of Patent: *Mar. 4, 2025**

(54) CHIMERIC VACCINE ANTIGENS FOR ANAPLASMOSIS

(71) Applicant: VIRGINIA COMMONWEALTH UNIVERSITY, Richmond, VA (US)

(72) Inventors: Richard T. Marconi, Midlothian, VA (US); Jason A. Carlyon, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 498 days.

This patent is subject to a terminal disclaimer.

(21) Appl. No.: 17/590,290

(22) Filed: Feb. 1, 2022

(65) Prior Publication Data

US 2022/0152180 A1 May 19, 2022

Related U.S. Application Data

(63) Continuation of application No. 17/048,296, filed as application No. PCT/US2019/027895 on Apr. 17, 2019, now Pat. No. 11,273,213.

(60) Provisional application No. 62/658,709, filed on Apr. 17, 2018.

(51) Int. Cl.

| | |
|---|---|
| ***A61K 39/02*** | (2006.01) |
| ***A61P 31/04*** | (2006.01) |
| ***A61P 37/04*** | (2006.01) |
| ***C07K 14/195*** | (2006.01) |

(52) U.S. Cl.
CPC .......... *A61K 39/0233* (2013.01); *A61P 31/04* (2018.01); *A61P 37/04* (2018.01); *C07K 14/195* (2013.01)

(58) Field of Classification Search
CPC ... C07K 14/195; A61K 39/0233; A61P 37/04; A61P 31/04
See application file for complete search history.

(56) References Cited

U.S. PATENT DOCUMENTS 11,273,213 B2 * 3/2022 Marconi ................ A61P 37/04

FOREIGN PATENT DOCUMENTS

WO WO-2015116907 A1 * 8/2015 ......... A61K 31/7088

* cited by examiner

*Primary Examiner* — Mary Maille Lyons
(74) *Attorney, Agent, or Firm* — WCF IP

(57) ABSTRACT

Provided herein are chimeric recombinant polypeptides (chimeritopes) for use in vaccines against Anaplasmosis, in assays for diagnosing Anaplasmosis and in assays for measuring antibody titers induced by vaccination. The chimeritopes comprise, for example, antigenic segments of three *Anaplasma* proteins (OmpA, AipA and Asp14) and a non-antigenic segment of a *Borrelia* Osp protein (e.g. OspC) that is 10 amino acids in length, proline rich and random coil in conformation. Compositions comprising the chimeritopes, optionally in combination with additional *Anaplasma* proteins of interest, are also provided, as are methods of using the compositions as vaccines and diagnostic tools.

2 Claims, 12 Drawing Sheets

Specification includes a Sequence Listing.

Amino acid sequence and physical properties of APH_1235 and P130 (APH_0032)

APH_1235

MKGKSDSEIR TSSSIRTSSS DDSRSSDDST RIRASKTHPQ APSDNSSILS
SEDIESVMRC LEEEYGQKLS SELKKSMREE ISTAVPELTR ALIPLLASAS
DSDSSSRKLQ EEWVKTFMAI MLPHMQKIVA STQG

Number of amino acids: 134
Molecular weight: 14771.47
Theoretical pI: 5.44

P130 (APH_0032)

MFEHNIPDTY TGTTAEGSPG LAGGDFSLSS IDFTRDFTIE SHRGSSADDP
GYISFRDQDG NVMSRFLDVY VANFSLRCKH SPYNNDRMET AAFSLTPDII
EPSALLQESH STQNNVEEAV QVTALECPPC NPVPAEEVAP QPSFLSRIIQ
AFLWLFTPSS TTDTAEDSKC NSSDTSKCTS ASSESLEQQQ ESVEVQPSVL
MSTAPIATEP QNAVVNQVNT TAVQVESSII VPESQHTDVT VLEDTTETIT
VDGEYGHFSD IASGEHNNDL PAMLLDEADF TMLLANEESK TLESMPSDSL
EDNVQELGTL PLQEGETVSE GNTRESLPTD VSQDSVGVST DLEAHSQEVE
TVSEVSTQDS LSTNISQDSV GVSTDLEAHS KGVEIVSEGG TQDSLSADFP
INTVESESTD LEAHSQEVET VSEFTQDSLS TNISQDSVGV STDLEVHSQE
VEIVSEGGTQ DSLSTNISQD SVGVSTDLEA HSQEVETVSE FTQDSLSTNI
SQDSVGVSTD LEVHSQEVEI VSEGGTQDSL STNISQDSVG VSTDLEAHSK
GVEIVSEGGT QDSLSADFPI NTVESESTDL EAHSPEGEIV SEVSTQDAPS
TGVEIRFMDR DSDDDVLAL

Number of amino acids: 619
Molecular weight: 66109.59
Theoretical pI: 3.80

Figure 4

Protein Induction In *E. coli*

Aph_1235 P130FL

Pre- Post Pre- Post

Purified proteins

MW Stds P130

MW Stds APH_1235

CHIMERIC VACCINE ANTIGENS FOR ANAPLASMOSIS

SEQUENCE LISTING

This application includes as the Sequence Listing the complete contents of the accompanying text file "Sequence.txt", created Apr. 16, 2019, containing 65,536 bytes, hereby incorporated by reference.

BACKGROUND OF THE INVENTION

Field of the Invention

The invention generally relates to recombinant chimeric polypeptides comprising epitopes derived from *Anaplasma* antigens. In particular, the invention provides i) recombinant chimeric epitope-based polypeptides (chimeritopes) comprising segments of three *Anaplasma* proteins (OmpA, AipA and Asp14) and a proline rich segment of a *Borrelia* protein or derivative thereof; and ii) compositions comprising the chimeritopes, optionally in combination with *Anaplasma* proteins P130 and APH_1235. The compositions are used as vaccines and diagnostic tools.

Description of Related Art

*Anaplasma phagocytophilum* (Aph) is a tick-transmitted, obligate intracellular bacterium of the family Anaplasmataceae. Several species of this family including *A. marginale, A. platys, Ehrlichia chaffeensis, E. canis*, and *E. ruminatium* can cause infections in humans, companion animals, livestock and wild animals Infections caused by this group of pathogens are generally referred to as "anaplasmosis" or "ehrlichiosis". In humans, the most serious form of anaplasmosis, referred to as human granculocytic anaplasmosis (HGA), is caused by Aph. Anaplasmosis is characterized by fever leukopenia, thrombocytopenia, elevated serum transaminase, and increased susceptibility to potentially fatal opportunistic infections. It is typically treated with doxycycline or tetracycline.

While antibiotics are generally effective for treatment, preventative strategies that can block infection, such as vaccination are preferable. Vaccination has historically proven to be the most cost-effective approach for the prevention of many infectious diseases. At the present time, there are no veterinary or human vaccines available for the prevention of *Anaplasma* and *Ehrlichia* infections. As the incidence of tick-borne disease continues to increase so is the demand for preventative vaccines. Here we detail the development of unique vaccine antigens and vaccine formulations that can address the growing problem of anaplasmosis and related infections. The deployment of an effective preventative vaccine will significantly advance veterinary and human health and alleviate the socioeconomic stress associated with tick-borne diseases.

The "gold standard" serologic test for diagnosis of HGA in humans is an indirect immunofluorescence assay (IFA). This assay must be performed at multiple time points over a period of several weeks and can only be performed in specialized reference laboratories. A limitation of the IFA assay is its specificity. The IFA is designed to assess increases in both IgM and IgG. While IgG antibody responses can be very specific, IgM responses are less so and have the potential to yield false-positive test results. Enzyme immunoassay (EIA) are also used for diagnosis. EIA tests are not quantitative and provide a simple positive or negative result. In veterinary medicine, lateral flow-based point of care assays are widely used for diagnosis of anaplasmosis and ehrlichiosis. It is clear that there is a pressing need for improved assays that are easier to conduct and that provide greater specificity and sensitivity.

SUMMARY OF THE INVENTION

Defined antigenic segments (i.e., epitopes) of three proteins produced by *Anaplasma* have been identified and demonstrated to play critical roles in the adherence and invasion of mammalian cells by *Anaplasma*. Recombinant chimeric polypeptides comprised of these epitopes have been successfully produced and demonstrated, upon vaccination, to elicit antibody responses that block *Anaplasma* entry into mammalian cells. The unique vaccine antigens that have been developed are referred to as "chimeritopes". Chimeritope stands for chimeric epitope-based proteins. The unique composition of chimeritope polypeptide/proteins differentiates this class of novel proteins from simple chimeric proteins. The term chimeric protein is most commonly used in reference to fusion proteins that are comprised of several different full-length proteins, or extended segments thereof, that are joined together to form a single contiguous protein. The distinction between a "chimeric protein" and a "chimeritope" is important because they are compositionally different. Chimeritopes are designed to only contain segments of a protein that are immunologically or functionally relevant (i.e., that elicit protective or neutralizing antibody responses).

Accordingly, the chimeritope vaccine antigens described herein are comprised of epitopes derived from at least three specific *Anaplasma* proteins: OmpA (Outer membrane protein A, AipA (Aph invasion protein A), and Asp14 (14-kDa Aph surface protein). The chimeritopes contain at least one copy of epitopes, or segments thereof, derived from the OmpA, AipA and Asp14 proteins. In some aspects, the carboxy terminus of each chimeritope includes a cap sequence having a random coil structure and a high proline content (e.g. 33% or greater) to protect the chimeritope from degradation. In additional aspects, the cap sequence is comprised of e.g. a 10 amino acid domain derived from a *Borrelia* protein such as PVVAESPKKP (SEQ ID NO: 5), or a functional variant thereof e.g. PVVPPSPKKP (SEQ ID NO: 6) or PVVPPSPPKP (SEQ ID NO: 7).

The chimeritopes are used as vaccine antigens to elicit protective antibody responses against *Anaplasma* (e.g. Aph) and other related bacteria. An advantage of chimeritopes is that they elicit antibody responses in vaccinated mammals to three independent targets that are presented on the surface of *Anaplasma* bacteria. By delivering the chimeritopes in combination with *Anaplasma* P130 and APH_1235, the synergistic effects of eliciting antibodies that target several different proteins are expanded. The chimeritopes are also used to detect antibody responses that develop during infection with *Anaplasma* or to measure antibody titers after vaccination with the AP chimeritopes.

Several different exemplary AP chimeritopes have been produced and tested for their immunogenicity and ability to block intracellular invasion of host cells by Aph. As detailed below, the chimeritopes have been assigned simple designations (AP1, AP2, AP3, AP4, etc.) to differentiate them. Specifically for the AP3 and AP4 chimeritopes, a second version of these proteins was made (v2). The v1 and v2 variants differ in that the order of a two amino acid motif is reversed in these variants. The designation v1 or v2 follows the AP # designation (i.e., AP3v1, AP3v2 etc). The purpose of generating the v1 and v2 AP proteins was to determine if minor changes in the amino acid sequence of one of the component epitopes (the OmpA epitope) influences functional activity.

The AP vaccine antigens provide protection through a unique mechanism. Antibodies that are produced as a result of vaccination or hyperimmmunization can bind to the surface of *Anaplasma* and block or attenuate it's ability adhere to and or enter mammalian cells. The vaccination-induced antibodies thus inhibit the ability of these obligate intracellular pathogens to establish an infection. A distinct and unique attribute of the AP chimeritopes, as opposed to common subunit single protein or protein chimeric based vaccines, is that the AP chimeritopes elicit antibody that binds to several different target proteins on the bacterial cell surface. The impact of antibody binding to multiple targets, as opposed to a single protein produced by the bacteria, is synergistic. Furthermore, by combining epitopes from multiple proteins into one protein, the cost of production is reduced and quality control and formulation strategies simplified. Embodiments of these recombinant AP chimeritope proteins delivered with or without additional Aph proteins (P130 and APH_1235) include preventive vaccines, passive and active therapeutic vaccines, diagnostic antigens and antigens for measuring vaccine induced antibody levels in vaccinated animals.

It is an object of this invention to provide a recombinant, chimeric polypeptide comprising, at least one copy of an invasion domain/epitope of *Anaplasma* OmpA, at least one copy of an invasion domain/epitope of *Anaplasma* AipA, and at least one copy of an invasion domain/epitope of *Anaplasma* Asp14. In some aspects, the invasion domain of *Anaplasma* OmpA has a sequence GKYDLKGPGKKVILELEVQL (SEQ ID NO: 1) and/or GKYDLKGPGKKVILELVEQL (SEQ ID NO: 2). In other aspects, the invasion domain of *Anaplasma* AipA has a sequence SLDPTQGSHTAENI (SEQ ID NO: 3). In additional aspects, the invasion domain of *Anaplasma* Asp14 has a sequence LKLERAVYGANTPKES (SEQ ID NO: 4). In yet further aspects, the recombinant chimeric polypeptide or polypeptides further comprise at least one copy of a cap sequence that is placed on the C-terminus of the chimeritopes to stabilize and protect against proteolytic degradation. A suitable cap sequence is a high proline, random coil, non-immunogenic sequence such as the 10 amino acid segment derived from the *Borellia* OspC protein. In some aspects, the C-terminal cap sequence motif is PVVAESPKKP (SEQ ID NO: 5). Other suitable cap sequences include but are not limited to PVVPPSPKKP (SEQ ID NO: 6). and PVVPPSPPKP (SEQ ID NO: 7).

In some aspects, the amino acid sequence of the recombinant, chimeric polypeptide is selected from the group consisting of:

```
(SEQ ID NO: 8)
GKYDLWGKYDLKGPGKKVILELEVQLSLDPTQGSH
TAENILKLERAVYGANTPKESLKLERAVYGANTPK
ESSLDPTQGSHTAENIGKYDLKGPGKKVILELEVQ
LSLDPTQGSHTAENIGKYDLKGPGKKVILELEVQL
LKLERAVYGANTPKESPVVAESPKKP;
```

-continued

```
(SEQ ID NO: 9)
GKYDLWGKYDLKGPGKKVILELVEQLSLDPTQGSH
TAENILKLERAVYGANTPKESLKLERAVYGANTPK
ESSLDPTQGSHTAENIGKYDLKGPGKKVILELVEQ
LSLDPTQGSHTAENIGKYDLKGPGKKVILELVEQL
LKLERAVYGANTPKESPVVAESPKKP;

(SEQ ID NO: 10)
LKLERWLKLERAVYGANTPKESGKYDLKGPGKKVI
LELEVQLSLDPTQGSHTAENIGKYDLKGPGKKVIL
ELEVQLSLDPTQGSHTAENILKLERAVYGANTPKE
SLKLERAVYGANTPKESSLDPTQGSHTAENIGKYD
LKGPGKKVILELEVQLPVVAESPKKP;

(SEQ ID NO: 11)
LKLERWLKLERAVYGANTPKESGKYDLKGPGKKVI
LELVEQLSLDPTQGSHTAENIGKYDLKGPGKKVIL
ELVEQLSLDPTQGSHTAENILKLERAVYGANTPKE
SLKLERAVYGANTPKESSLDPTQGSHTAENIGKYD
LKGPGKKVILELVEQLPVVAESPKKP;

(SEQ ID NO: 12)
GKYDLWGKYDLKGPGKKVILELEVQLSLDPTQGSH
TAENILKLERAVYGANTPKESGKYDLKGPGKKVIL
ELEVQLSLDPTQGSHTAENILKLERAVYGANTPKE
SGKYDLKGPGKKVILELEVQLSLDPTQGSHTAENI
LKLERAVYGANTPKESPVVAESPKKP;

(SEQ ID NO: 13)
GKYDLWGKYDLKGPGKKVILELVEQLSLDPTQGSH
TAENILKLERAVYGANTPKESGKYDLKGPGKKVIL
ELVEQLSLDPTQGSHTAENILKLERAVYGANTPKE
SGKYDLKGPGKKVILELVEQLSLDPTQGSHTAENI
LKLERAVYGANTPKESPVVAESPKKP;

(SEQ ID NO: 14)
GKYDLWGKYDLKGPGKKVILELEVQLGKYDLKGPG
KKVILELEVQLGKYDLKGPGKKVILELEVQLSLDP
TQGSHTAENISLDPTQGSHTAENISLDPTQGSHTA
ENILKLERAVYGANTPKESLKLERAVYGANTPKES
LKLERAVYGANTPKESPVVAESPKKP;

(SEQ ID NO: 15)
GKYDLWGKYDLKGPGKKVILELVEQLGKYDLKGPG
KKVILELVEQLGKYDLKGPGKKVILELVEQLSLDP
TQGSHTAENISLDPTQGSHTAENISLDPTQGSHTA
ENILKLERAVYGANTPKESLKLERAVYGANTPKES
LKLERAVYGANTPKESPVVAESPKKP;
```

-continued (SEQ ID NO: 16)
GKYDLWGKYDLKGPGKKVILELEVQLSLDPTQGSH
TAENILKLERAVYGANTPKESLKLERAVYGANTPK
ESSLDPTQGSHTAENIGKYDLKGPGKKVILELEVQ
LSLDPTQGSHTAENIGKYDLKGPGKKVILELEVQL
LKLERAVYGANTPKES;

(SEQ ID NO: 17)
GKYDLWGKYDLKGPGKKVILELVEQLSLDPTQGSH
TAENILKLERAVYGANTPKESLKLERAVYGANTPK
ESSLDPTQGSHTAENIGKYDLKGPGKKVILELVEQ
LSLDPTQGSHTAENIGKYDLKGPGKKVILELVEQL
LKLERAVYGANTPKES;

(SEQ ID NO: 18)
LKLERWLKLERAVYGANTPKESGKYDLKGPGKKVI
LELEVQLSLDPTQGSHTAENIGKYDLKGPGKKVIL
ELEVQLSLDPTQGSHTAENILKLERAVYGANTPKE
SLKLERAVYGANTPKESSLDPTQGSHTAENIGKYD
LKGPGKKVILELEVQL;

(SEQ ID NO: 19)
LKLERWLKLERAVYGANTPKESGKYDLKGPGKKVI
LELVEQLSLDPTQGSHTAENIGKYDLKGPGKKVIL
ELVEQLSLDPTQGSHTAENILKLERAVYGANTPKE
SLKLERAVYGANTPKESSLDPTQGSHTAENIGKYD
LKGPGKKVILELVEQL;

(SEQ ID NO: 20)
GKYDLWGKYDLKGPGKKVILELEVQLSLDPTQGSH
TAENILKLERAVYGANTPKESGKYDLKGPGKKVIL
ELEVQLSLDPTQGSHTAENILKLERAVYGANTPKE
SGKYDLKGPGKKVILELEVQLSLDPTQGSHTAENI
LKLERAVYGANTPKES;

(SEQ ID NO: 21)
GKYDLWGKYDLKGPGKKVILELVEQLSLDPTQGSH
TAENILKLERAVYGANTPKESGKYDLKGPGKKVIL
ELVEQLSLDPTQGSHTAENILKLERAVYGANTPKE
SGKYDLKGPGKKVILELVEQLSLDPTQGSHTAENI
LKLERAVYGANTPKES;

(SEQ ID NO: 22)
GKYDLWGKYDLKGPGKKVILELEVQLGKYDLKGPG
KKVILELEVQLGKYDLKGPGKKVILELEVQLSLDP
TQGSHTAENISLDPTQGSHTAENISLDPTQGSHTA
ENILKLERAVYGANTPKESLKLERAVYGANTPKES
LKLERAVYGANTPKES;
and -continued (SEQ ID NO: 23)
GKYDLWGKYDLKGPGKKVILELVEQLGKYDLKGPG
KKVILELVEQLGKYDLKGPGKKVILELVEQLSLDP
TQGSHTAENISLDPTQGSHTAENISLDPTQGSHTA
ENILKLERAVYGANTPKESLKLERAVYGANTPKES
LKLERAVYGANTPKES.

In further aspects, the amino acid sequence of the recombinant, chimeric polypeptide is:

(SEQ ID NO: 13)
GKYDLWGKYDLKGPGKKVILELVEQLSLDPTQGSH
TAENILKLERAVYGANTPKESGKYDLKGPGKKVIL
ELVEQLSLDPTQGSHTAENILKLERAVYGANTPKE
SGKYDLKGPGKKVILELVEQLSLDPTQGSHTAENI
LKLERAVYGANTPKESPVVAESPKKP.
or (SEQ ID NO: 15)
GKYDLWGKYDLKGPGKKVILELVEQLGKYDLKGPG
KKVILELVEQLGKYDLKGPGKKVILELVEQLSLDP
TQGSHTAENISLDPTQGSHTAENISLDPTQGSHTA
ENILKLERAVYGANTPKESLKLERAVYGANTPKES
LKLERAVYGANTPKESPVVAESPKKP.

Also provided are pharmaceutical compositions comprising at least one recombinant, chimeric polypeptide listed above. In some aspects, the pharmaceutical composition, further comprises one or both of: MKGKSDSEIR TSSSIRTSSS DDSRSSDDST RIRASKTHPQ APSDNSSILS SEDIESVMRC LEEEYGQKLS SELKKSMREE ISTAVPELTR ALIPLLASAS DSDSSSRKLQ EEWVKTFMAI MLPHMQKIVA STQG (SEQ ID NO: 25; APH_1235), and MFEHNIPDTY TGTTAEGSPG LAGGDFSLSS IDFTRDFTIE SHRGSSADDP GYISFRDQDG NVMSRFLDVY VANFSLRCKH SPYNNDRMET AAFSLTPDII EPSALLQESH STQNNVEEAV QVTALECPPC NPVPAEEVAP QPSFLSRIIQ AFLWLFTPSS TTDTAEDSKC NSSDTSKCTS ASSESLEQQQ ESVEVQPSVL MSTAPIATEP QNAVVNQVNT TAVQVESSII VPESQHTDVT VLEDTTETIT VDGEYGHFSD IASGEHNNDL PAMLLDEADF TMLLANEESK TLESMPSDSL EDNVQELGTL PLQEGETVSE GNTRESLPTD VSQDSVGVST DLEAHSQEVE TVSEVSTQDS LSTNISQDSV GVSTDLEAHS KGVEIVSEGG TQDSLSADFP INTVESESTD LEAHSQEVET VSEFTQDSLS TNISQDSVGV STDLEVHSQE VEIVSEGGTQ DSLSTNISQD SVGVSTDLEA HSQEVETVSE FTQDSLSTNI SQDSVGVSTD LEVHSQEVEI VSEGGTQDSL STNISQDSVG VSTDLEAHSK GVEIVSEGGT QDSLSADFPI NTVESESTDL EAHSPEGEIV SEVSTQDAPS TGVEIRFMDR DSDDDVLAL (SEQ ID NO: 24; P130), and/or a subfragment or segment thereof. In certain aspects, the subfragment of SEQ ID NO: 24 is or includes residues 163 to 619.

Also provided are methods of eliciting an immune response to *Anaplasma* in a subject in need thereof, comprising administering to the subject an amount of the pharmaceutical composition as described herein that is sufficient to elicit an immune response in the subject.

In some aspects, the immune response is a protective immune response.

Also provided are methods of blocking or attenuating the binding of *Anaplasma* to mammalian cells in a subject in need thereof, comprising administering to the subject a pharmaceutical composition as described herein, wherein the pharmaceutical composition is administered in an amount sufficient to elicit the production of antibodies that block or attenuate the binding of *Anaplasma* to mammalian cells in the subject.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

FIG. 4. The amino acid sequences and basic properties of APH_1235 and P130 (APH_0032). The sequences of the P130 (SEQ ID NO: 24) and APH_1235 (SEQ ID NO: 25) proteins were analyzed using ProtParam (see the website at web.expasy.org/protparam). The ProtParam analyses provide important information about the general properties of proteins. P130 (also referred to in the literature as APH_0032, GE130, or AmpB) contributes to Aph virulence and survival in host cells. APH_1235 is expressed by the bacterium at high levels exclusively when it is in its infectious or dense core (DC) form. P130 and APH_1235 are important virulence factors. Based on the role that these proteins play in virulence and their overall properties, these proteins were produced and purified for inclusion in the vaccine formulation. Analyses detailing the enhanced protection that results from co-delivering these proteins along with AP3 and or AP4 as a vaccine formulation are detailed below.

DETAILED DESCRIPTION

Figure 1A:
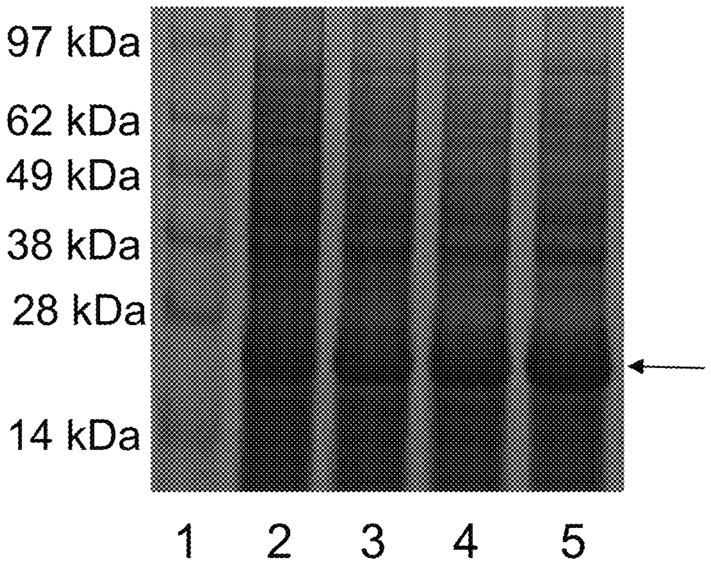
FIGS. 1A and B. Expression of AP3v2 in *E. coli*. Plasmids encoding the AP3v2 protein (SEQ ID NO: 12) were transformed into *Escherichia coli* strains and protein production induced. Aliquots of culture were collected over time (lanes 2-5) and the cell lysates fractionated using a 4-12% SDS-polyacrylamide gel. (A) shows the induction profile for sample ZRL309 (*E. coli* BL21(DE3)Star cells carrying the pET28b-AP3v2 plasmid) and (B) shows the induction profile of sample ZRL311 (*E. coli* BL21 carrying the pFLEX30/AP3v2 plasmid). The proteins were visualized by staining. The arrow indicates the migration position of the AP3v2 chimeritope. Molecular weight (MW) standards are shown in lane 1. The results demonstrate that Ap3v2 can be readily expressed in *E. coli* using different plasmid expression vectors.

The present disclosure provides novel anti-*Anaplasma* vaccine antigens that were developed using "chimeritope technology" i.e. they are chimeric epitope based recombinant polypeptides. The disclosure further provides two Aph proteins (P130 and APH_1235) that when (optionally) delivered in combination with the novel chimeritopes enhance the protective efficacy of the vaccine formulation. Vaccines which include the chimeritopes are designed to block the ability of *Anaplasma* to bind to mammalian cells, and enter or invade those cells. Because *Anaplasma* is an obligate intracellular bacterium (i.e. it cannot survive freely outside of eukaryotic cells), lessening the ability of *Anaplasma* to invade mammalian cells also leads to killing *Anaplasma*. As described below in the Examples section, the vaccine antigens have been successfully produced, and their immunogenicity has been demonstrated in vivo. In addition, antibodies raised to these chimeric proteins attenuate (e.g. decrease or lessen) *Anaplasma* adherence to and invasion of mammalian cells, and thus decrease the ability of *Anaplasma* bacteria to infect mammalian cells, and/or increase the ability to clear an existing infection. In some aspects, the chimeritopes are used e.g. in vaccine compositions that may or may not also include the APH P130 and APH_1235 proteins, polypeptides or antigenic fragments thereof.

Definitions

"*Anaplasma*" as used herein refers to a genetically related group of bacteria that includes *A. phagocytophilum, A. marginale, A. platys, E. chaffeensis, E. canis, E. ruminatium*, and other antigenically related or similar species.

Epitope: the part of a protein or antigen that is capable of eliciting an immune response (antibody production) and that is capable of binding the specific antibody produced by such a response. Epitopes are commonly referred to as the antigenic determinants of a protein. Immunodominant epitope: The epitope on a molecule that induces a dominant, or most intense, immune response. The immunodominant epitope may elicit, for example, the greatest antibody titer during infection or immunization, as measured by, for example, the fraction of reactivity attributable to a certain antigen or epitope in an enzyme-linked immunosorbant assay as compared with the total responsiveness to an antigen set or entire protein.

Chimeritope: custom designed recombinant polypeptides created in the laboratory that are comprised of epitopes and/or specific protein segments derived from multiple different proteins or protein variants. In sharp contrast to natural antigenic proteins, chimeritopes can be designed to elicit antibodies that can target several different protein targets and several different species of one or more genera of bacteria that cause disease in mammals. For example, the chimeritopes described herein elicit antibodies that target numerous proteins produced by numerous species of *Anaplasma* that cause anaplasmosis in mammals, such as humans, companion animals, wild canids, wildlife and others. Chimeritopes may be referred to herein as "recombinant, chimeric polypeptides", "recombinant AP chimeritope proteins", "recombinant chimeritope constructs", etc.

Designed: The term "designed" as used herein refers to an amino acid sequence of a recombinant, chimeric polypeptide ("chimeritope"), or of an individual epitope, that is altered as described herein, and therefore is unlike a native amino acid sequence. The term "designed" refers to the property that such chimeritopes are man-made, synthetic and not from nature. Instead, they are non-naturally occurring and are the result of an inventive procedure. Further, the phrase "not from nature" means that the sequence is not present as a non-artificial sequence entry in a sequence database, for example in GenBank, EMBL-Bank or Swiss-Prot. These databases and other similar sequence databases are well known to the person skilled in the art.

Invasion domain: An invasion domain is a region of a surface protein of a pathogen that binds a host cell and mediates pathogen entry into the host cell. In some cases, uptake of the pathogen results in the formation of a vacuole in which the intracellular pathogen will reside. The invasion domains of the disclosure are linear amino acid sequences within Asp14, OmpA, or AipA that are found on the outer membrane of the bacteria Aph and other Anaplasmataceae family members, and can vary slightly from one family member to the next. Invasion domains may be referred to herein as "epitopes".

Linker sequences: short peptide sequences encoding functional units that may be engineered or otherwise added at the ends or within recombinant proteins, polypeptides, peptides of interest. Linker sequences may be used as "handles" for protein purification, as detectable signals of expression or binding to other proteins or macromolecules, to modulate tertiary structure, enhance immunogenicity or to protect against proteolytic degradation of a recombinant protein. Examples of linker sequences include but are not limited to an amino acid spacer, an amino acid linker, a signal sequence, a stop transfer sequence, a transmembrane domain, a domain of a protein that separates two epitopes, and a C- or N-terminal protein cap.

LINKER: a program to generate linker sequences for fusion proteins. Protein Engineering 13(5): 309-312, which is a reference that describes unstructured linkers. Structured (e.g. helical) sequence linkers may also be designed using, for example, existing sequences that are known to have that secondary structure, or using basic known biochemical principles to design the linkers.

Tags: Recombinant amino acid sequences that can be added to the N- or C-terminus of a recombinant protein for the purpose of identification or for purifying the recombinant protein for subsequent uses. Examples of recombinant protein tags that may be useful in practicing the invention include but are not limited to glutathione-S-transferease (GST), poly-histidine, maltose binding protein (MBP), FLAG, V5, halo, myc, hemaglutinin (HA), S-tag, calmodulin, tag, streptavidin binding protein (SBP), SOFTAG1™, SOFTAG3™, Xpress tag, isopeptag, Spy Tag, biotin carboxyl carrier protein (BCCP), GFP, Nus-tag, strep-tag, thioredoxin tag, TC tag, and Ty tag. All such tags are well-known to those of ordinary skill in the art of recombinant protein production.

Chimeric or fusion peptide/polypeptide: a recombinant or synthetic peptide or polypeptide whose primary sequence comprises two or more linear amino acid sequences which do not occur together in a single molecule in nature. The two or more sequences may, for example, encode fusions of full-length proteins or fusions of extended polypeptides, or two or more peptides (which may be the same or different) which are either contiguous or separated by a linker sequences, etc.

Tandem repeats: two or more copies of nucleic acid or amino acid sequences encoding the same peptide, which are arranged in a linear molecule and are either contiguous or separated by a linker sequences, etc.

Original, native or wild-type sequence: The sequence of a peptide, polypeptide, protein or nucleic acid as found in nature.

Recombinant peptide, polypeptide, protein or nucleic acid: peptide, polypeptide, protein or nucleic acid that has been removed from its native source (or is a copy of a sequence from a native source) and produced and/or manipulated using molecular biology/genetic engineering techniques such as cloning, polymerase chain reaction (PCR), etc.

Synthetic peptide, polypeptide, protein or nucleic acid: peptide, polypeptide, protein or nucleic acid that has been produced using chemical synthesis procedures.

The Constructs

The *Anaplasma* chimeritope constructs disclosed herein comprise antigenic segments, or variants thereof, of at least three proteins: *Anaplasma* proteins OmpA, AipA and Asp14. In addition, in some aspects, the proteins possess a cap sequence (e.g. a 10 amino acid cap sequence) at their C-terminus. The cap sequence may be derived from e.g. a *Borrelia* outer surface protein or another suitable protein, or may be entirely synthetically designed with no natural counterpart. Exemplary segments and/or variants thereof that are present in the chimeritopes are listed in Table 1 below, together with an indication of the origin, an assigned number or letter designation and the associated SEQ ID NO.

TABLE 1

| Origin | Designation | Sequence | SEQ ID NO: |
|---|---|---|---|
| *Anaplasma* OmpA | #1 OmpA | GKYDLKGPGKKVILELEVQL | 1 |
| | | GKYDLKGPGKKVILELVEQL | 2 |
| *Anaplasma* AipA | #2 AipA | SLDPTQGSHTAENI | 3 |
| *Anaplasma* Asp14 | #3 Asp14 | LKLERAVYGANTPKES | 4 |
| *Borrelia* Osp | #C-C10 | PVVAESPKKP | 5 |
| Exemplary variant of SEQ ID NO: 5 | | PVVPPSPKKP | 6 |
| Exemplary variant of SEQ ID NO: 5 | | PVVPPSPPKP | 7 |

In some aspects, the recombinant chimeritope construct has a single copy of each antigenic segment joined together in a polypeptide. However, to facilitate production and/or to increase antigenicity, generally multiple copies of each *Anaplasma* segment are present. Thus, multiple copies of one or more of each segment may be present, e.g. from about 1 to about 20 copies of each, such as about 1, 2, 3, 4, 5, 6, 7, 8, 9, 10, 11, 12, 13, 14, 15, 16, 17, 18, 19, or 20 copies. In some aspects, the recombinant polypeptides encompassed herein comprise from e.g. at least about 1 to about 5 or more copies (e.g. about 1, 2, 3, 4, or 5 or more copies) of the #1 OmpA, #2 AipA and #3 Asp14 epitopes.

The number of copies of each *Anaplasma* based segment that is present may or may not be the same for all segments. For example, two copies of each of #1 OmpA and #2 AipA may be present in a recombinant construct that has 3 or 4 copies of #3 Asp14; or one copy of #3 Asp14 may be present in a construct that comprises 2 copies of #1 OmpA and 4 copies of #2 AipA, and so on. All such constructs are encompassed herein. In some aspects, 3 copies of each of #1 OmpA, #2 AipA and #3 Asp14 are present in a construct. Generally only one copy of #C-C10 (or a variant thereof) is present in each protein. The function of the C10 segment is to provide a protective cap at the C-terminus that is non-immunogenic, and that inhibits proteolytic degradation of the chimeritope proteins.

The *Anaplasma* epitopes may be in any linear order in a chimeritope, i.e. the position of one or more epitopes and/or other elements within a construct may be "swapped" or "exchanged", compared to the exemplary proteins disclosed herein. For example, the order of the one or more copies of the segments may be, when reading from the segment nearest to the amino terminus of the protein toward the carboxyl terminus: #1 OmpA, #2 AipA, #3 Asp14; or #2 AipA, #1 OmpA, #3 Asp1; or #3 Asp1, #2 AipA, #1 OmpA; and so on. Further, if multiple copies of a segment are present, they may be present in tandem, e.g. #1 OmpA, #1 OmpA, #1 OmpA; #2 AipA, #2 AipA, #2 AipA; #3 Asp14, #3 Asp14, #3 Asp14; etc.; or they may not be in tandem, e.g. they may be interspersed within other segments, e.g. #1 OmpA, #2 AipA, #3 Asp14; #1OmpA, #2 AipA, #3 Asp14; #1OmpA, #2 AipA, #3 Asp14; etc.

The amino acid sequences of the antigenic segments and the exemplary chimeritopes disclosed herein may be altered and still be suitable for use. In other words, the sequences need not be identical to the sequences as disclosed herein by SEQ ID NO. For example, certain conservative amino acid substitutions are made without having a deleterious effect on the ability of an individual epitope or a chimeritope as a whole to elicit an immune response, e.g. a protective immune response. A conservative substitution is one in which an amino acid is substituted for another amino acid that has similar properties, such that one skilled in the art of peptide chemistry would expect the secondary structure and hydropathic nature of the polypeptide to be substantially unchanged. In some exemplary aspects, the following groups of amino acids represent conservative exchanges/substitutions: aliphatic (glycine, alanine, valine, leucine, isoleucine); hydroxyl or sulfur/selenium-containing (serine, cysteine, selenocysteine, threonine, methionine); aromatic (e.g. phenylalanine, tyrosine, tryptophan); basic (histidine, lysine, arginine); and acidic (aspartate, glutamate) and their amides (asparagine glutamine) For example, conservative substitutions such as the following may be tolerated: substitution of one positively charged amino acid for another positively charged amino acid; substitution of a negatively charged amino acid for another negatively charged amino acid; substitution of a hydrophobic amino acid for another hydrophobic amino acid; etc. In fact, the results presented herein have demonstrated that other non-conservative minor alterations of amino acid sequence (e.g. the reversal of the sequence EV to VE) do not inhibit or alter the ability of the AP proteins to elicit Ab that can block infection. Specifically, this was demonstrated by comparing immune responses of AP3v1 with AP3v2 and AP4v1 with AP4v2 (see Table 1). All such substitutions, alterations or variants are encompassed herein, as long as the resulting sequence still functions to elicit a suitable immune response, and/or to detect antibodies in biological samples, as described herein.

Versions of the sequences presented herein with one or more deletions are also encompassed, e.g. versions from which about 1-5 (e.g. about 1, 2, 3, 4, or 5) consecutive amino acids have been deleted, are also encompassed, as long as the physiological function of the individual epitope, or the full length chimeritope (e.g. the ability to elicit an immune response and/or detect antibodies in biological samples) is not impaired. Such deletions may be truncations e.g. located at the amino or carboxyl terminus, or internal deletions within a sequence.

In addition, in some aspects, altered or variant sequences may contain an insertion of e.g. from about 1-5 amino acids (e.g. 1, 2, 3, 4, or 5 amino acids), and still be tolerated, as long as the physiological function of the individual epitope, or the full length chimeritope (e.g. the ability to elicit an immune response), is not impaired. Insertions may be made e.g. at the amino terminus, the carboxyl terminus, within a sequence, or between epitope sequences.

Amino acid sequences that are substituted, truncated or have an insertion are typically referred to herein as "based on" or "derived from" or "variants of" the original sequence.

Examples of changes/variations include but are not limited to: elimination or introduction of a protease cleavage site; elimination or introduction of a lipidation sequence; changes which increase or decrease solubility (e.g. changes to hydrophobicity, etc.); changes which increase or decrease intra- or inter-molecular interactions such as folding, ionic interactions, salt bridges, the formation of disulfide bonds, the formation of multimers (e.g. dimers, trimers, etc.); and so on, which are effected by adding or removing one or more amino acids that participate in such interactions. In some aspect, the changes avoid or decrease such interactions; in other aspects, the changes promote or increase such interactions. For example, the introduction of one or more cysteine residues can permit the formation of disulfide bridges within a sequence, thereby stabilizing the sequence, e.g. in vivo. Similarly, the introduction of one or more lipidation sequences may confer desirable properties such as optimal folding, antigenicity, solubility, etc. Changes may be introduced which prevent interference with the presentation and accessibility of the individual epitopes along the length of the chimera, or which increase such accessibility, e.g. placement of a sequence at the surface of a folded construct. All such changes are intended to be encompassed by the present invention, so long as the resulting amino acid sequence functions to elicit an immune response, e.g. a protective immune response, in at least one targeted mammalian population.

In general, altered (variant) sequences exhibit at least about 50% to 99% identity or similarity to a corresponding sequence in the native protein, e.g. about 60 to 70, or 70 to 80, or 80 to 90, or 90 to 99% identity/similarity (e.g. about 90, 91, 92, 93, 94, 95, 96, 98, or 99%) to the wild type sequence. "Identity" defines the percentage of amino acids with a direct match in a sequence alignment; percent similarity of two sequences is the sum of both identical and similar matches (residues that have similar properties). In other words, percent identity refers to the percentage of identical residues while percent similarity refers to the percentage of residues with similar physicochemical properties. In some aspects, the altered sequence is about 95 to 100% identical or similar, e.g. about 95, 96, 97, 98 or 99% identical/similar. Variant polypeptides may have one or more conservative amino acid variations or other minor modifications and retain biological activity, i.e., are biologically functional equivalents. A biologically active equivalent has substantially equivalent function when compared to the corresponding original polypeptide. For example, as shown herein AP3v1 and Ap3v2 as well as AP4v1 and AP4v2 are biologically functional equivalents (e.g., replacing the EV motif with VE did not affect immunological properties).

Percent sequence identity or similarity has an art recognized meaning and there are a number of methods to measure identity/similarity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J. Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used.

Variant polypeptides can generally be identified by modifying one of the polypeptide sequences of the disclosure, and evaluating the properties of the modified polypeptide to determine if it is a biological equivalent. A variant is a biological equivalent if it retains e.g. 90% or greater, of the activity of the original polypeptide (e.g. retains the ability to elicit an immune response and/or bind to *Anaplasma* antibodies), as measured e.g. in a competition assay wherein the biologically equivalent polypeptide is capable of reducing binding of the polypeptide of the disclosure to a corresponding reactive antigen or antibody by about 80, 85, 90, 95, 99, or 100%.

In some aspects, the individual epitopes in the chimeritopes are separated from one another by one or more intervening sequences that are not associated with an epitope disclosed herein in nature and are substantially neutral in character and, i.e. they do not necessarily in and of themselves elicit an immune response. Such sequences may or may not be present between the epitopes. An amino acid spacer can comprise e.g. about 1, 5, 10, 20, 100, or 1,000 amino acids. If present, they may, for example, separate the epitopes and contribute to steric isolation of the epitopes from each other. Alternatively, such sequences may be simply artifacts of recombinant processing procedures, e.g. cloning procedures. Such sequences are typically known as linker or spacer peptides (elements, sequences), many examples of which are known to those of skill in the art. Suitable peptide linker sequences may be chosen, for example, based on the following factors: 1) the ability to adopt a flexible extended conformation; 2) the resistance to adopt a secondary structure that could interact with epitopes; and 3) the lack of hydrophobic or charged residues that might react with the epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in, for example, Maratea et al., Gene, 1985, 40, 39-46; Murphy et al., Proc. Natl. Acad. Sci. USA, 1986, 83, 8258-8262; and U.S. Pat. No. 4,935,233, the complete contents of which is herein incorporated by reference in entirety; Crasto, C. J. and J. A. Feng. 2000; LINKER: a program to generate linker sequences for fusion proteins; Protein Engineering 13(5): 309-312, which is a reference that describes unstructured linkers. Structured (e.g. helical) sequence linkers may also be designed using, for example, existing sequences that are known to have that secondary structure, or using basic known biochemical principles to design the linkers.

Other elements may be present in the chimeritopes, for example signal or leader sequences that co-translationally or post-translationally direct transfer of the protein and/or sequences that "tag" the protein to facilitate purification or detection of the protein. Examples of such elements include but are not limited to: tryptophan residues, histidine tags, glutathione-S-transferase, trpE, maltose binding protein, Staphylococcal protein A, detection tags (e.g. S-tag, or Flag-tag), other antigenic amino acid sequences such as known Tv2ell epitope containing sequences, protein stabilizing motifs, sequences that enhance binding of the polypeptide to a solid support (e.g. an immunoglobulin Fc region or bovine serum albumin), etc Amino terminus protecting groups such as acetyl, propyl, succinyl, benzyl, benzyloxycarbonyl or t-butyloxycarbonyl may be present, as may carboxyl terminus protecting groups such as amide, methylamide, and ethylamide. In addition, the chimeric proteins may be chemically modified, e.g. by amidation, sulfonylation, lipidation, or other techniques that are known to those of skill in the art. Polypeptide stability can be enhanced by adding, for example, polyethylene glycol to the amino or carboxyl terminus of the polypeptide.

In another iteration, a bacterial lipidation motif or isolated Cys residue could be added to the N-terminus of the protein to allow for its lipidation. The attachment of a lipid group can in some cases trigger stronger antibody responses.

An amino acid sequence as disclosed herein can also be linked to a moiety (i.e., a functional group that is a polypeptide or other compound) that enhances an immune response (e.g., cytokines such as IL-2).

A chimeritope may also be designed to contain W (tryptophan) residues with or without additional accompanying amino acid residues that are not naturally found in the epitopes used to make the protein. The purpose of including the W residue(s) is to make the protein detectable by UV and thus make quantitation of the protein easier and more accurate. Generally, such a W residue is introduced near the N-terminus of a construct but could also be introduced at the juncture of individual epitopes within the chimeritopes constructs. Examples of suitable short, W containing sequences include, but are not limited to: LKLERW (SEQ ID NO: 6) and GKYDLW (SEQ ID NO: 7). Note that the context in which the W is introduced (i.e., alone or with one or more amino acid residues) does not need to be strictly defined as any sequence including a W could be used and it can vary in length.

A chimeritope can also have an amino acid or chemical moiety attached at one or both of its termini (N- and C-terminus) that functions to stabilize the protein and to protect the protein from proteolytic degradation. We refer to such a protective sequence or moiety as a "cap". Generally, cap sequences are about 10 amino acids in length (e.g. from about 5 to about 15 amino acids, such as about 5, 6, 7, 8, 9, 10, 11, 12, 13, 14, or 15 amino acids). A typical cap sequence is rich in proline (e.g. is about 25 to 40% proline, such as about 25, 30, 35, or 40% proline, such as about 33% proline) and adopts a random coil confirmation. Also, cap sequences are typically not immunogenic. In some aspects, the constructs include the cap sequence PVVAESPKKP (SEQ ID NO: 5). This sequence is derived from the last ten amino acid residues of a *Borrelia* Osp protein. It is added to the AP proteins to provide a C-terminal cap to protect against proteolytic degradation. This sequence is particularly useful for this purpose because it is not immunogenic and thus does not elicit irrelevant antibody responses. Variants of this sequence are also encompassed, e.g. variants such as PVVPPSPKKP (SEQ ID NO: 6). and PVVPPSPPKP (SEQ ID NO: 7).

Exemplary Constructs

The sequences shown below represent examples of the recombinant chimeritopes disclosed herein. It is noted that the difference between the "v1" AP chimeritope constructs and the "v2" AP chimeritopes constructs is that the v1 constructs contain the EV sequence at the underlined positions of the Omp epitope while the v2 constructs contain the sequence VE at those positions. Sequences containing a W and sequences from a *Borrelia* Osp are shown in bold.

AP1v1 construct: 1-2-3-3-2-1-2-1-3-C (note that the numbers listed indicate the specific epitopes and their order in each construct; the numbering used is detailed in Table 1 above)

(SEQ ID NO: 8)

GKYDLWGKYDLKGPGKKVILELEVQLSLDPTQGSH

TAENILKLERAVYGANTPKESLKLERAVYGANTPK

-continued

ESSLDPTQGSHTAENIGKYDLKGPGKKVILELEVQ

LSLDPTQGSHTAENIGKYDLKGPGKKVILELEVQL

LKLERAVYGANTPKESPVVAESPKKP.

AP1v2 construct: 1-2-3-3-2-1-2-1-3-C (SEQ ID NO: 9)

GKYDLWGKYDLKGPGKKVILELVEQLSLDPTQGSH

TAENILKLERAVYGANTPKESLKLERAVYGANTPK

ESSLDPTQGSHTAENIGKYDLKGPGKKVILELVEQ

LSLDPTQGSHTAENIGKYDLKGPGKKVILELVEQL

LKLERAVYGANTPKESPVVAESPKKP.

AP2v 1 construct: 3-1-2-1-2-3-3-2-1-C (SEQ ID NO: 10)

LKLERWLKLERAVYGANTPKESGKYDLKGPGKKVI

LELEVQLSLDPTQGSHTAENIGKYDLKGPGKKVIL

ELEVQLSLDPTQGSHTAENILKLERAVYGANTPKE

SLKLERAVYGANTPKESSLDPTQGSHTAENIGKYD

LKGPGKKVILELEVQLPVVAESPKKP.

AP2v2 construct: 3-1-2-1-2-3-3-2-1-C (SEQ ID NO: 11)

LKLERWLKLERAVYGANTPKESGKYDLKGPGKKVI

LELVEQLSLDPTQGSHTAENIGKYDLKGPGKKVIL

ELVEQLSLDPTQGSHTAENILKLERAVYGANTPKE

SLKLERAVYGANTPKESSLDPTQGSHTAENIGKYD

LKGPGKKVILELVEQLPVVAESPKKP.

AP3v1 construct: 1-2-3-1-2-3-1-2-3-C (SEQ ID NO: 12)

GKYDLWGKYDLKGPGKKVILELEVQLSLDPTQGSH

TAENILKLERAVYGANTPKESGKYDLKGPGKKVIL

ELEVQLSLDPTQGSHTAENILKLERAVYGANTPKE

SGKYDLKGPGKKVILELEVQLSLDPTQGSHTAENI

LKLERAVYGANTPKESPVVAESPKKP.

AP3v2 construct: 1-2-3-1-2-3-1-2-3-C (SEQ ID NO: 13)

GKYDLWGKYDLKGPGKKVILELVEQLSLDPTQGSH

TAENILKLERAVYGANTPKESGKYDLKGPGKKVIL

ELVEQLSLDPTQGSHTAENILKLERAVYGANTPKE

SGKYDLKGPGKKVILELVEQLSLDPTQGSHTAENI

LKLERAVYGANTPKESPVVAESPKKP.

AP4v1 construct: 1-1-1-2-2-2-3-3-3-C (SEQ ID NO: 14)

GKYDLWGKYDLKGPGKKVILELEVQLGKYDLKGPG

KKVILELEVQLGKYDLKGPGKKVILELEVQLSLDP

TQGSHTAENISLDPTQGSHTAENISLDPTQGSHTA

ENILKLERAVYGANTPKESLKLERAVYGANTPKES

LKLERAVYGANTPKESPVVAESPKKP.

-continued

AP4v2 construct: 1-1-1-2-2-2-3-3-3-C
(SEQ ID NO: 15)
GKYDLWGKYDLKGPGKKVILELVEQLGKYDLKGPG
KKVILELVEQLGKYDLKGPGKKVILELVEQLSLDP
TQGSHTAENISLDPTQGSHTAENISLDPTQGSHTA
ENILKLERAVYGANTPKESLKLERAVYGANTPKES
LKLERAVYGANTPKESPVVAESPKKP.

AP5v1 construct: 1-2-3-3-2-1-2-1-3
(SEQ ID NO: 16)
GKYDLWGKYDLKGPGKKVILELEVQLSLDPTQGSH
TAENILKLERAVYGANTPKESLKLERAVYGANTPK
ESSLDPTQGSHTAENIGKYDLKGPGKKVILELEVQ
LSLDPTQGSHTAENIGKYDLKGPGKKVILELEVQL
LKLERAVYGANTPKES.

AP5v2 construct: 1-2-3-3-2-1-2-1-3
(SEQ ID NO: 17)
GKYDLWGKYDLKGPGKKVILELVEQLSLDPTQGSH
TAENILKLERAVYGANTPKESLKLERAVYGANTPK
ESSLDPTQGSHTAENIGKYDLKGPGKKVILELVEQ
LSLDPTQGSHTAENIGKYDLKGPGKKVILELVEQL
LKLERAVYGANTPKES.

AP6v1 construct: 3-1-2-1-2-3-3-2-1
(SEQ ID NO: 18)
LKLERWLKLERAVYGANTPKESGKYDLKGPGKKVI
LELEVQLSLDPTQGSHTAENIGKYDLKGPGKKVIL
ELEVQLSLDPTQGSHTAENILKLERAVYGANTPKE
SLKLERAVYGANTPKESSLDPTQGSHTAENIGKYD
LKGPGKKVILELEVQL.

AP6v2 construct: 3-1-2-1-2-3-3-2-1
(SEQ ID NO: 19)
LKLERWLKLERAVYGANTPKESGKYDLKGPGKKVI
LELVEQLSLDPTQGSHTAENIGKYDLKGPGKKVIL
ELVEQLSLDPTQGSHTAENILKLERAVYGANTPKE
SLKLERAVYGANTPKESSLDPTQGSHTAENIGKYD
LKGPGKKVILELVEQL.

AP7v1 construct: 1-2-3-1-2-3-1-2-3
(SEQ ID NO: 20)
GKYDLWGKYDLKGPGKKVILELEVQLSLDPTQGSH
TAENILKLERAVYGANTPKESGKYDLKGPGKKVIL
ELEVQLSLDPTQGSHTAENILKLERAVYGANTPKE
SGKYDLKGPGKKVILELEVQLSLDPTQGSHTAENI
LKLERAVYGANTPKES.

AP7v2 construct: 1-2-3-1-2-3-1-2-3
(SEQ ID NO: 21)
GKYDLWGKYDLKGPGKKVILELVEQLSLDPTQGSH
TAENILKLERAVYGANTPKESGKYDLKGPGKKVIL
ELVEQLSLDPTQGSHTAENILKLERAVYGANTPKE -continued

SGKYDLKGPGKKVILELVEQLSLDPTQGSHTAENI
LKLERAVYGANTPKES.

AP8v1 construct: 1-1-1-2-2-2-3-3-3
(SEQ ID NO: 22)
GKYDLWGKYDLKGPGKKVILELEVQLGKYDLKGPG
KKVILELEVQLGKYDLKGPGKKVILELEVQLSLDP
TQGSHTAENISLDPTQGSHTAENISLDPTQGSHTA
ENILKLERAVYGANTPKESLKLERAVYGANTPKES
LKLERAVYGANTPKES.

AP8v2 construct: 1-1-1-2-2-2-3-3-3
(SEQ ID NO: 23)
GKYDLWGKYDLKGPGKKVILELVEQLGKYDLKGPG
KKVILELVEQLGKYDLKGPGKKVILELVEQLSLDP
TQGSHTAENISLDPTQGSHTAENISLDPTQGSHTA
ENILKLERAVYGANTPKESLKLERAVYGANTPKES
LKLERAVYGANTPKES.

Other Sequences of Interest

Also provided are additional specific *Anaplasma* (e.g. Aph) proteins and polypeptides that may be used to elicit or enhance an immune response as described herein. These include the exemplary sequences depicted in FIGS. 4A and B (referred to herein as APH_1235, SEQ ID NO: 25, and P130 (APH_0032) SEQ ID NO: 24, as well as variants and antigenic segments or epitopes thereof. P130 (also referred to in the literature as APH_0032, GE130, or AmpB) contributes to Aph virulence and survival in host cells. APH_1235 is expressed by the bacterium exclusively when it is in its infectious or dense core (DC) form, and contributes to infectivity. These proteins/polypeptides, and/or subfragments thereof, may be used alone e.g. in vaccine compositions, as diagnostic tools, etc. as described herein, or one or both of the sequences may be used in combination with one or more chimeritopes. In some aspects, a subfragment of P130 is used, e.g. the exemplary segment spanning a C-terminal portion of the protein from residues 163 to 619, inclusive, of SEQ ID NO: 24. This segment is referred to herein as P130C.

Nucleic Acids and Vectors

Also encompassed by this disclosure are nucleic acid sequences that encode the amino acid sequences disclosed herein. Such nucleic acids sequences include DNA, RNA, DNA/RNA hybrids, complementary DNA (cDNA), species homologs and variant sequences, and the like. In some aspects, the nucleic acids sequences are DNA.

In some aspects, the nucleic acid sequences presented herein are codon optimized for a particular production system, e.g. they may be codon optimized to eliminate rare codons that interfere with production in a bacterial expression system. For example, the eight least used codons of *Escherichia coli* shown below with the amino acids they encode, can be eliminated:

| | |
|---|---|
| AGG | arginine |
| AGA | arginine |
| AUA | isoleucine |
| CUA | leucine |
| CGA | arginine |
| CGG | arginine |
| CCC | proline |
| UCG | |

The nucleic acid sequences may comprise or be operably linked to various noncoding regulatory elements and/or expression related sequences, examples of which include but are not limited to: stop transfer sequences, expression control sequences, expression enhancing sequences, etc. Methods for preparing polynucleotides operably linked to an expression control sequence and expressing them in a host cell are known in the art. See, e.g., U.S. Pat. No. 4,366,246, the complete contents of which is hereby incorporated by reference in entirety. A polynucleotide of the disclosure is operably linked when it is positioned adjacent to or close to one or more expression control elements, which direct transcription and/or translation of the polynucleotide.

In addition, the disclosure encompasses vectors which contain or house the nucleic acid sequences. Examples of suitable vectors include but are not limited to plasmids, cosmids, viral based vectors, expression vectors, etc. In some aspects, PCR amplicons are used for production of the proteins in a bacterial system.

Production of Proteins

The chimeritopes disclosed herein may be produced by any suitable method, many of which are known to those of skill in the art. For example, the proteins may be chemically synthesized, or produced using recombinant DNA technology i.e. produced by organisms or cells that are genetically engineered to produce the proteins. Exemplary organisms and cells include but are not limited to bacterial cells; mammalian, yeast and insect cells; plants and plant cells, etc. In addition, production may also be via cell-free prokaryotic or eukaryotic-based transcription/translation systems, or by other in vitro systems, etc.

Compositions

The disclosure also provides compositions (pharmaceutical compositions such as immunogenic compositions, vaccines and compositions for use in diagnostic assays) comprising the chimeritopes disclosed herein and, optionally, one or more additional sequences of interest such as SEQ ID NOS: 25 and 26, for use in eliciting an immune response to *Anaplasmataceae* species. The compositions generally include one or more types of substantially purified chimeritopes as described herein, and a pharmacologically suitable carrier. In other words, the chimeritopes in the composition may all be the same, or may be different so that the composition is a "cocktail" of different types of chimeritopes. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, phosphate buffered saline, Ringer's solution, Hank's solution, maltodextrin, ethanol, or the like, singly or in combination, as well as substances such as wetting agents, emulsifying agents, tonicity adjusting agents, detergent, or pH buffering agents. Additional active agents, such as bactericidal agents can also be used. Pharmaceutically acceptable salts can also be used in compositions of the disclosure, for example, mineral salts such as hydrochlorides, hydrobromides, phosphates, or sulfates, as well as salts of organic acids such as acetates, proprionates, malonates, or benzoates.

If it is desired to administer an oral form of the composition, various thickeners, flavorings, diluents, emulsifiers, dispersing aids or binders and the like may be added. The composition of the present disclosure may contain any such additional ingredients so as to provide the composition in a form suitable for administration. The final amount of chimeric protein in the formulations may vary. However, in general, the amount in the formulations will be from about 0.01-99%, weight/volume.

The vaccine preparations of the present disclosure may further comprise one or more adjuvants, suitable examples of which include but are not limited to: mineral salts, alum (multiple different substituted variants), squalene-based adjuvants (e.g. MF59 adjuvant), muramyl peptide, saponin derivatives, *mycobacterium* cell wall preparations, certain emulsions, monophosphoryl lipid A, mycolic acid derivatives, nonionic block copolymer surfactants, QUIL A®, cholera toxin B subunit, polyphosphazene and derivatives, immunostimulating complexes (ISCOMs), cytokine adjuvants, lipid adjuvants, mucosal adjuvants, certain bacterial exotoxins and other components, certain oligonucleotides, PLG, SEPPIC™, ALHYDRAGEL®, CpG, cyclic-di-GMP, Freund's adjuvant and others.

Dosage forms of the compositions are also encompassed, especially single dose forms that are suitable for use as a vaccine. The dosage forms may be injectable, inhalable or oral, depending on the intended route of administration.

Antibodies

The disclosure also encompasses antibodies and antigen binding fragments thereof that bind to at least one of the recombinant polypeptides described herein. In particular, the antibodies bind specifically, or at least selectively, to at least one epitope in the recombinant polypeptides. For example, an antibody or antigen-binding portion thereof specifically binds to a polypeptide when it exhibits a binding affinity $K_a$ of $10^7$ l/mol or more. Specific binding can be tested using, for example, surface plasmon resonance, an enzyme-linked immunosorbant assay (ELISA), a radioimmunoassay (RIA), a dot-blot, a slot-blot or a western blot assay using methodology well known in the art.

The antibodies may also bind to a variant polypeptide or a fragment of a polypeptide, so long as the variant or fragment contains at least one *Anaplasma* epitope that is or is biologically equivalent to an epitope disclosed herein. The antibodies may be polyclonal, monoclonal, single chain antibodies (scFv), or antigen binding fragments thereof, e.g. a portion of an intact antibody comprising the antigen binding site or variable region of an intact antibody, but free of the constant heavy chain domains of the Fc region. Examples include Fab, Fab', Fab'-SH, $F(ab')_2$ and $F_v$ fragments. The antibodies may be of any class, including, for example, IgG, IgM, IgA, IgD and IgE and/or any subclass, IgG1, IgG2 etc.

An antibody can be made in vivo in suitable laboratory animals or in vitro using recombinant DNA techniques. Means for preparing and characterizing antibodies are well known in the art. See, e.g., Dean, Methods Mol. Biol. 80:23-37 (1998); Dean, Methods Mol. Biol. 32:361-79 (1994); Baileg, Methods Mol. Biol. 32:381-88 (1994); Gullick, Methods Mol. Biol. 32:389-99 (1994); Drenckhahn et al. Methods Cell. Biol. 37:7-56 (1993); Morrison, Ann. Rev. Immunol. 10:239-65 (1992); Wright et al. Crit. Rev. Immunol. 12:125-68 (1992). For example, polyclonal antibodies can be produced by administering a polypeptide of the disclosure to an animal, such as a human or other primate, mouse, rat, rabbit, guinea pig, goat, pig, dog, cow, sheep, donkey, or horse. Serum from the immunized animal is collected and the antibodies are purified from the plasma. Techniques for producing and processing polyclonal antibodies are known in the art.

In particular, monoclonal antibodies directed against epitopes present in a polypeptide can be readily produced. For example, normal B cells from a mammal, such as a mouse, which was immunized with a polypeptide can be fused with, for example, HAT-sensitive mouse myeloma cells to produce hybridomas. Hybridomas producing specific antibodies can be identified using radioimmunoassay (RIA) and/or ELISA and isolated by cloning in semi-solid agar or by limiting dilution. Clones producing specific antibodies are isolated by another round of screening. Monoclonal antibodies can be screened for specificity using standard techniques, for example, by binding a polypeptide of interest to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., P.N.A.S. U.S.A. 82:8653 1985; Spria et al., J. Immunolog. Meth. 74:307, 1984. Monoclonal antibodies of the disclosure can also be recombinant monoclonal antibodies. See, e.g., U.S. Pat. Nos. 4,474,893; 4,816,567. Antibodies can also be chemically constructed. See, e.g., U.S. Pat. No. 4,676,980.

Accordingly, also encompassed are methods of producing (generating) antibodies to the antigenic sequences disclosed herein. Such methods may include steps of 1) providing or obtaining at least one antigenic chimeritope as disclosed herein; 2) administering the chimeritope to a mammal that is capable of generating antibodies to the chimeritope; and after a period of time sufficient for an antibody-generating immune response to occur within the mammal, 3) harvesting antibodies from the mammal.

Antibodies that specifically bind the antigens disclosed herein are particularly useful for detecting the presence of *Anaplasma* antigens in a sample, such as a serum, blood, plasma, urine, fecal, tissue, or saliva sample from a subject, e.g. a mammal. An immunoassay for *Anaplasma* antigens can utilize one antibody or several different antibodies Immunoassay protocols can be based upon, for example, competition, direct reaction, or sandwich type assays using, for example, labeled antibody. Antibodies of the disclosure can be labeled with any type of label known in the art, including, for example, fluorescent, chemiluminescent, radioactive, enzyme, colloidal metal, radioisotope and bioluminescent labels. Other antibodies of the disclosure can specifically bind Aph antigens and Apl (*A. platys*) antigens, or Aph antigens and other *Anaplasma* spp. antigens, and can be used as described herein for antibodies that bind to Aph.

Methods

Methods of Eliciting an Immune Response

The disclosure also provides methods of eliciting an immune response to *Anaplasma* by administering a composition comprising one or more types of the chimeritope proteins disclosed herein. The composition is generally administered in an amount sufficient to elicit an immune response, e.g. a therapeutic dose is administered. An immune response (reaction) is a response to an antigen that occurs when lymphocytes identify the antigenic molecule as foreign and induce the formation of antibodies and lymphocytes capable of reacting with it and, in some aspects, rendering it harmless. In this activation process the main cells involved are T cells and B cells (sub-types of lymphocytes), and macrophages (a type of leucocyte or white blood cell). These cells produce cytokines that influence the activity of other immune cells. B cells, when activated by helper T cells undergo clonal expansion and differentiate into effector B cells, which are short lived and secrete antibodies, and memory B cells, which are long lived and produce a fast, remembered response when exposed to the same infection in the future. B cells mature to produce immunoglobulins (also known as antibodies), that react with (bind to) antigens. At the same time, macrophages process antigens into immunogenic units that can stimulate B lymphocytes to differentiate into antibody-secreting plasma cells, stimulating the T cells to release lymphokines. Complement is a group of normal serum proteins that enhance the immune response by becoming activated as the result of antigen-antibody interaction. The first contact with any antigen sensitizes the affected individual and promotes a primary immune response. Subsequent exposure of a sensitized individual to the same antigen results in a more rapid and massive reaction, called the secondary immune response ("booster response" or the "anamnestic reaction"). An anamnestic response manifests in the form of increased levels of circulating antibody.

Thus, methods of administering the compositions described herein may include e.g. an initial administration, followed by follow-up administrations at suitable time intervals, e.g. after about 3 to 12 weeks, and/or after about 6 months, and also optionally e.g. annually, or every 5 or 10 years thereafter to maintain a high level of protection.

The vaccine preparations of the present disclosure, or the nucleotides that encode them, may be administered by any of the many suitable means which are well known to those of skill in the art, including but not limited to: by injection, inhalation, orally, intranasally, intradermal injection as part of a DNA based vaccine, by ingestion of a food product containing the chimeric protein, etc. In general, the mode of administration is subcutaneous, intramuscular or oral. In addition, the compositions may be administered in conjunction with other treatment modalities such as substances that boost the immune system, chemotherapeutic agents (e.g. antibiotics), and the like.

The chimeritopes disclosed herein elicit an immune response when administered to a subject. Generally, the immune response involves the elements described above, including the elicitation of antibodies. In some aspects, the immune response is a protective immune response, i.e. after at least one administration of one dose of a vaccine preparation as described herein, and typically after two or more doses are administered, if the vaccinated individual is exposed to an infectious agent comprising the antigens present in a chimeritope (e.g. an *Anaplasmataceae* bacteria), the subject's immune system recognizes and destroys the infectious agent before an infection is established. In other aspects, the immune response may not be fully protective, but at least slows or decreases the level of infection established by the bacterium.

The vaccines are useful to inoculate naïve individuals (those who have not been exposed to or infected by *Anaplasmataceae* bacteria) and can also be beneficial to those who have been exposed and/or who are already infected. For example, administration of the vaccine may curb the potential of the bacteria to establish an infection, or may slow or gradually eradicate bacteria already present in the individual, thereby lessening one or more symptoms of disease.

Diagnostic Methods

The chimeritopes of the disclosure can be used to detect antibodies or antibody fragments specific for *Anaplasma* spp. in a test sample, such as a biological sample, an environmental sample, or a laboratory sample, from a subject. A biological sample can include, for example, sera, saliva, blood, cells, plasma, urine, feces, or tissue from a mammal such as a horse, cat, dog or human. The test sample can be untreated, precipitated, fractionated, separated, diluted, concentrated, or purified. Subjects who are tested using these methods may be asymptomatic or symptomatic with respect to exhibiting symptoms of anaplasmosis.

In one aspect, methods of the disclosure comprise contacting one or more recombinant polypeptides of the disclosure with a test sample under conditions that allow antigen/antibody complexes, i.e., immune complexes, to form between the polypeptides and antibodies that are present in the sample, and then detecting the complexes. Assays and conditions that are used to detect antibody/polypeptide complexes are generally known in the art.

Alternatively, antibodies disclosed herein can be used in a method of diagnosing *Anaplasma* infection in a subject e.g., a human or animal suspected of having an *Anaplasma* infection. A suitable test sample is obtained from the subject and the test sample is contacted with one or more antibodies under conditions enabling the formation of antibody-antigen complexes between the antibodies and *Anaplasma* bacteria (or fragments or polypeptides thereof) and then detecting the complexes. Assays and conditions that are used to detect antibody/polypeptide complexes are generally known in the art.

The detection of antigen/antibody complexes is an indication that the mammal has an *Anaplasma* infection whereas the absence of immune complexes represents a negative result. The amount of antibody/antigen complex can be determined by methodology known in the art, and comparisons to positive and negative controls are generally employed, e.g. to establish a frame of reference, to establish as baseline, etc.

In some aspects, the antigen/antibody are detected indirectly when an indicator reagent or detectable label comprising a signal generating moiety is detected, e.g. a chromophore or enzyme substrate that is attached directly or indirectly to the polypeptide/antibody complexes. Those of skill in the art are familiar with such detection schemes, e.g. colorimetric labels, second and third anti-species antibodies, the use of enzymes and enzyme substrates, etc. Assays of the disclosure include, but are not limited to those based on competition, direct reaction or sandwich-type assays, including, but not limited to enzyme linked immunosorbent assay (ELISA), dot blot, slot blot, western blot, IFA, radioimmunoassay (RIA), hemagglutination (HA), fluorescence polarization immunoassay (FPIA), and microtiter plate assays (any assay done in one or more wells of a microtiter plate).

Assays can use solid phases or substrates or can be performed by immunoprecipitation or other methods that do not utilize solid phases. Where a solid phase or substrate is used, one or more recombinant polypeptides or antibodies of the disclosure are directly or indirectly attached to a solid support or a substrate such as a microtiter well, magnetic bead, non-magnetic bead, bar, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). The substrate materials are used in suitable shapes, such as films, sheets, or plates, or are coated onto or bonded or laminated to appropriate inert carriers, such as paper, glass, plastic films, or fabrics. Suitable methods for immobilizing peptides on solid phases include ionic, hydrophobic, covalent interactions and the like.

The formation of a polypeptide/antibody complex or an immunocomplex/indicator complex can be detected by e.g., radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The label is capable of producing a detectable signal either by itself or in conjunction with one or more additional substances.

Formation and detection of antigen/antibody is indicative of the presence of anti-*Anaplasma* spp. antibodies in the sample (if the recombinant chimeritopes are used in the assay) or of the presence of *Anaplasma* spp. in the sample (if antibodies are used in the assay). Either way, the methods of the disclosure are used to diagnose anaplasmosis in a subject. The methods of the disclosure can also indicate the amount or quantity of anti-*Anaplasma* spp. antibodies or *Anaplasma* spp. in a test sample. Generally, the amount of antibody complex that is present is proportional to the signal generated.

The disclosure further comprises assay kits (e.g., articles of manufacture) for detecting levels of circulating antibody that were induced by vaccination, anti-*Anaplasma* spp. antibodies or antigen-binding antibody fragments in a sample. A kit comprises one or more chimeritopes of the disclosure and means for determining binding of the chimeritopes to anti-*Anaplasma* spp. antibodies or antigen-binding antibody fragments in the sample; and/or anti-*Anaplasma* antibodies generated against the chimeritopes disclosed herein. Other components such as buffers, controls, and the like, known to those of ordinary skill in art, are generally included in such test kits.

In addition, the assays described herein may include reagents that detect other pathogens, e.g. heartworm and/or *B. burgdorferi, E. chaffeensis*, and/or *E. canis*. Thus, an assay may detect multiple pathogens in a single sample.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1. Expression and Production of Recombinant AP3v2 and AP4v2

The DNA sequences that encode for AP3v2 and AP4v2 chimeric proteins were codon-optimized, synthesized, and cloned into expression vectors pET28b (MilliporeSigma; Burlington, MA) and pFLEX30 (proprietary to Zoetis) by Blue Heron Biotech (Bothell, WA). pFLEX30 utilizes a heat-inducible promotor for expression of the target protein. Each construct encodes for a N-terminal 6× His tag, which allows for purification of the expressed protein via a $Ni^{2+}$ column. Plasmid constructs containing sequences encoding for AP3v2 and AP4v2 were transformed into *E. coli* expression hosts BL21(DE3)Star (for pET28b) and BL21 (for pFLEX30). Designations for the constructs are as follows:

*ZRL*309=*BL*21(*DE*3)Star/*pET*28*b*/*AP*3*v*2

*ZRL*310=*BL*21(*DE*3)Star/*pET*28*b*/*AP*4*v*2

*ZRL*311=*BL*21/*p*FLEX30/*AP*3*v*2

*ZRL*312=*BL*21/*p*FLEX30/*AP*4*v*2

Figure 1B:
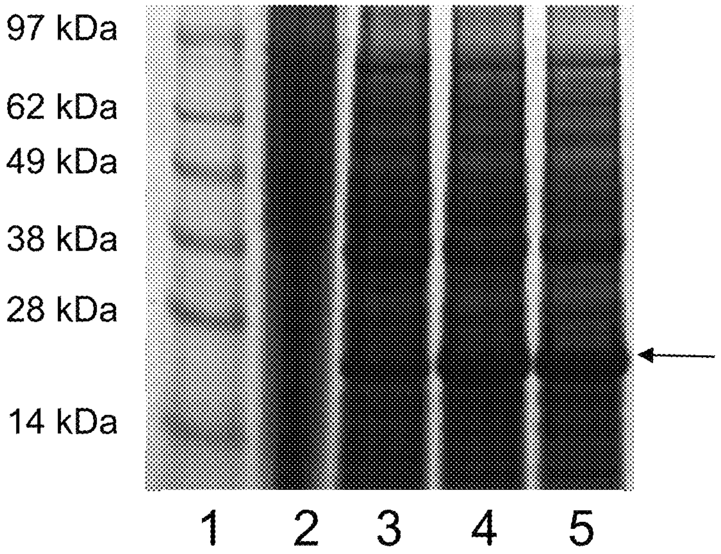
Figure 2A:
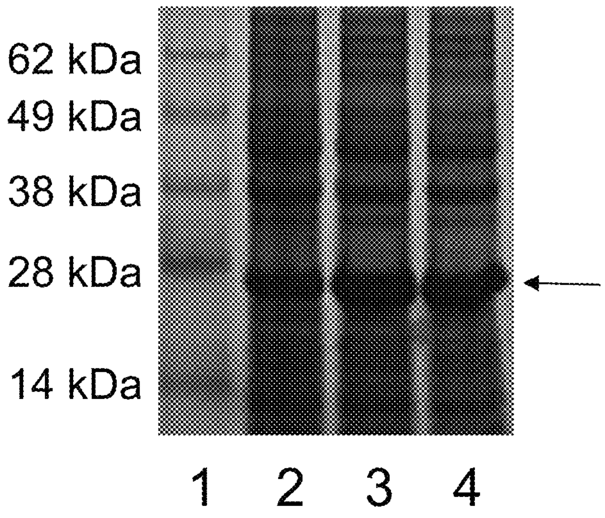
FIGS. 2A and B. Expression of AP4v2 in *E. coli*. Plasmids encoding the AP4v2 protein (SEQ ID NO: 14) were transformed into *E. coli* strains and protein production induced. Aliquots of culture were removed over time and fractionated using a 4-12% SDS-polyacrylamide gel. (A, lanes 2-4) and (B, lanes 2-6) show the protein profiles for samples ZRL310 (*E. coli* BL21(DE3)Star) cells carrying the pET28b-AP4v2 plasmid) and ZRL312 (*E. coli* BL21 carrying the pFLEX30/AP4v2 plasmid). Proteins were visualized by staining. The arrow indicates the migration position of the recombinant AP4v2 chimeritope. Purified AP4v2 is shown in lane 6. Molecular weight (MW) standards are shown in lane 1. The results demonstrate that Ap4v2 can be readily expressed in *E. coli* using different plasmid expression vectors. Further, the produced protein is stable and was readily purified to homogeneity.
Figure 2B:
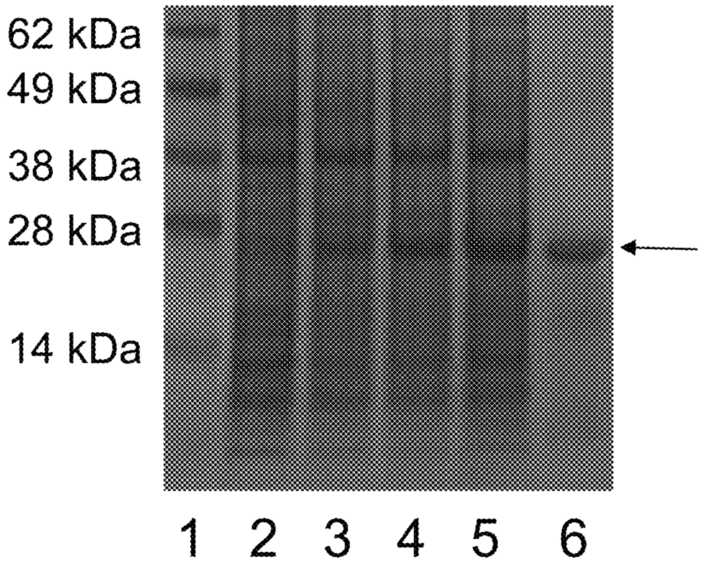

All initial expression studies were carried out in Terrific Broth (Teknova; Hollister, CA) containing 50 ug/ml kanamycin, at the 100 ml scale in baffled shake flasks while shaking at 200 RPM. These studies were followed by larger scale (500 ml) expression in TB using 2 L baffled shake flasks. All pET28b constructs were propagated at 37° C. to an ~$OD_{600}$ 3.0, at which time they were induced with 1 mM IPTG (Time 0; T0). All pFLEX30 constructs were propagated at 33° C. to an ~$OD_{600}$ 3.0, followed immediately by a 42° C. heat induction at T0. All pFLEX30 and pET28b cultures were allowed to continue growing for an additional 2 or 3 hrs post-induction. The cells were then recovered by centrifugation (10 min, 8,500×G) and frozen (−20° C.). As needed the frozen samples were thawed, mixed with solubilizing solution and boiled. Samples were evaluated for production of the recombinant proteins by electrophoresis on Novex precast 4-12% SDS PAGE gels (ThermoFisher Scientific; Waltham, MA). Protein production over time was monitored. The results for AP3v2 are shown in FIGS. 1A and 1B, and the results for AP4v2 are shown in FIGS. 2A and 2B. pET28b expression of both AP proteins appeared to be "leaky", as small amounts of AP3v2 and AP4v2 were visible prior to IPTG induction. The pFLEX30 expression system was therefore used for further cloning and protein production due to the ability to better control expression from this vector.

Figure 3:
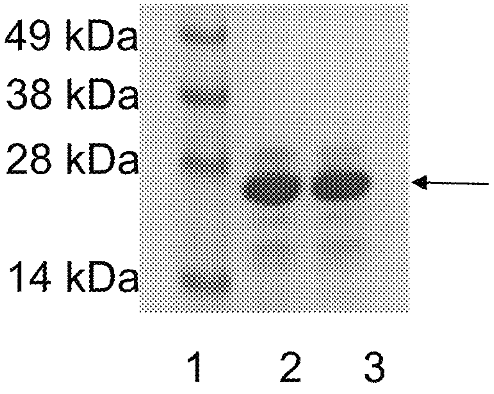
FIG. 3. SDS-PAGE analysis of purified AP4v2. AP4v2 (SEQ ID NO: 14) derived from ZRL312 was purified and dialyzed into PBS. The protein was electrophoresed on a 4-12% SDS-polyacrylamide gel. MW markers are indicated in lane 1 and the purified protein is shown in lane 2. Lane 3 shows the purified protein after passage through a 0.2 um-sterilization filter. The arrow indicates the migration position of the recombinant AP4v2 chimeritope. The data demonstrate that Ap4v2 can be readily purified and that the protein is amenable to the sterilizing filtration steps that are required in vaccine production.

To purify the chimeritope proteins, frozen cell pellets were resuspended in 200 mls of 50 mM Tris HCl (pH 8.0). Re-suspended cells were lysed by passing once through an Avestin C3 cell disruptor (Avestin Inc.; Ottawa, ON, Canada) at 25,000 PSI. Following homogenization, the lysed cell slurry was centrifuged at 10,000×G for 30 min at 4° C. Once spun supernatant was poured off, the pellet was re-suspended in equilibration buffer (50 mM Tris; 10 mM NaCl; 6M Urea; 10 mM imidazole, pH 8.0) and loaded onto a Ni SEPHAROSE™ Excel 5 mL XK16 column (GE Healthcare Life Sciences; Pittsburgh, PA), and purified using the ÄKTA™ pure protein purification system (GE Healthcare Life Sciences). The column was washed with equilibration buffer until absorption of UV light was at baseline. Elution was then conducted using a 0-100% B gradient over 5 column volumes using an elution buffer (50 mM Tris; 10 mM NaCl; 6M Urea; 500 mM imidazole, pH 8.0). Fractions were collected and select fractions were pooled and dialyzed into 50 mM Tris 10 mM NaCl (pH 8.0). The Ap3v2 protein (before and after filtration through a 0.2 um filter) is shown in FIG. 3. The results demonstrate that the proteins can be readily purified and that their yield and integrity is not affected by sterilization filtration.

Example 2. Cloning, Expression, Purification and Antigenicity of APH_1235 and P130

Figure 5A:
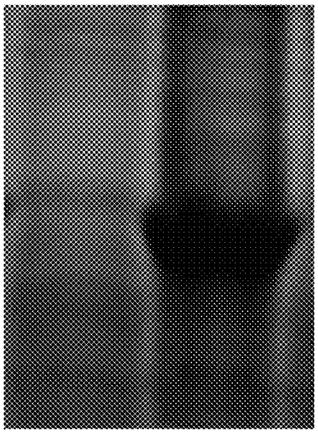
FIGS. 5A-D. Expression of APH_1235 and P130 in *E. coli*. Genes encoding the APH_1235 (SEQ ID NO: 25) and P130 (SEQ ID NO: 24) proteins were cloned and protein production induced (A) and (B), respectively. Prior to induction, and 6 hrs post-induction, aliquots of each culture were analyzed by SDS-PAGE using ANYkDa precast gels (Bio-rad). Proteins were visualized by staining. Cell lysates from pre- and post-induction are shown in lanes 1 and lane 2, respectively of (A) and (B). The chimeritope proteins were then purified and reassessed by SDS-PAGE. Purified APH_1235 and P130 are shown in (C) and (D) respectively (Lane 1=MW markers and Lane 2=purified protein). Arrows indicate the migration positions of the APH_1235 and P130 proteins in each figure. Both proteins were successfully produced and purified allowing for their assessment as vaccine candidates.
Figure 5B:
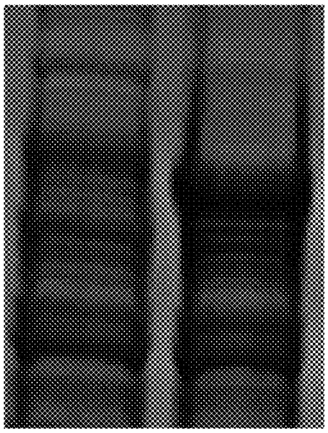
Figure 5C:
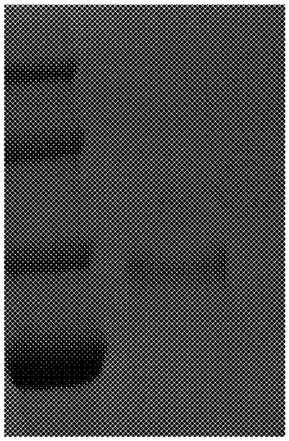
Figure 5D:
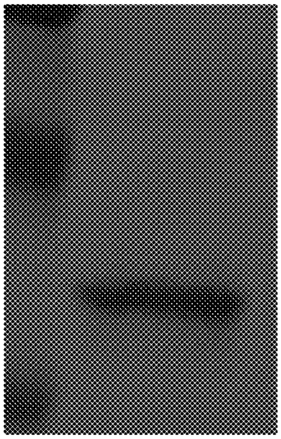

APH_1235, full-length P130 (P130FL) and a C-terminal antigenic domain of P130 were PCR amplified from previous cloning vectors and annealed with linearized pET45 Ligase Independent Cloning vector used standard conditions. The annealed DNA was transformed into *E. coli* NOVABlue cells, and the plasmids propagated. The plasmids were then purified and introduced into *E. coli* BL21/DE3 cells. Protein production was induced using IPTG. Cell lysates from pre and post-induced cultures were fractionated by SDS-PAGE and the gels stained to visualize the proteins. FIGS. 5A and 5B show the induction results for the APH_1235 and P130FL proteins, respectively (data not shown for P130C). After determining that the proteins fractionated into the soluble phase of the cell lysates, the proteins were purified using and AKTA purification platform and $Ni^{2+}$ affinity chromatography; they were then analyzed by SDS-PAGE electrophoresis (FIGS. 5C and 5D). Note that the amino acid sequences of APH_1235 and P130 are shown in FIG. 4 for reference.

Figure 6A:
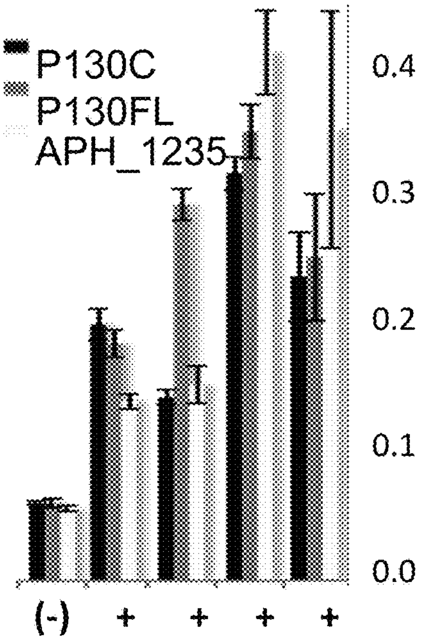
FIGS. 6A and B. Demonstration that the P130 and APH_1235 proteins are antigenic during natural infection in client owned canines. To determine if naturally infected client owned dogs develop antibody against the P130 (SEQ ID NO: 24) and APH_1235 (SEQ ID NO: 25) proteins, single dilution ELISA analyses were conducted. APH_1235 and two versions of the P130 protein were screened (A): i) full length P130 (SEQ ID NO: 24), referred to in FIG. 6A as "P130FL"; and ii) P130C, a subfragment of P130 spanning a C-terminal portion of the protein (residues 163 to 619 of SEQ ID NO: 24). The reason for generating and testing the C-terminal fragment of P130 stems from the presence of high probability antigenic determinants in this region. The recombinant chimeritope polypeptides, AP3v1 (SEQ ID NO: 12) and AP4v1 (SEQ ID NO: 14) were also analyzed (B). The proteins were immobilized in the wells of 96 well ELISA plates using standard ELISA methods and screened with serum from healthy (−) or Aph-infected (+) dogs. Absorbance was read using a plate reader at a wavelength of 405 nM (A405). A405 values are shown for each figure. Note that for the analyses of the AP3v1 and AP4v1 proteins, the Aph P44 protein was included as a positive control for antibody binding. The AP proteins were screened with serum from purpose-bred beagles that were experimentally infected with Aph. These analyses demonstrate that the P130 and APH_1235 are antigenic during a natural infection. Importantly, the results in (B) demonstrate that the domains/epitopes selected for inclusion in the AP proteins do elicit significant antibody responses as presented by Aph cells. This finding provides further supporting evidence for their inclusion in the chimeritopes.

Recombinant P130C (C-terminal domain), P130FL (full-length protein) or APH_1235 (full-length protein) were screened by standard single dilution ELISA with serum from healthy or Aph infected dogs. The proteins were immobilized in the wells of ELISA plates, non-specific binding was blocked and the canine serum samples were added at a 1:200 dilution. Antibody binding was detected using horseradish peroxidase conjugated goat anti-canine IgG secondary antibody, and chemiluminescence (FIG. 6A). These data demonstrate that infected canines develop an IgG response to P130 (both full length and C-terminal domains) and APH_1235 during natural infection. These results demonstrate that the P130 and APH_1235 proteins are antigenic during infection in canines.

Figure 6B:
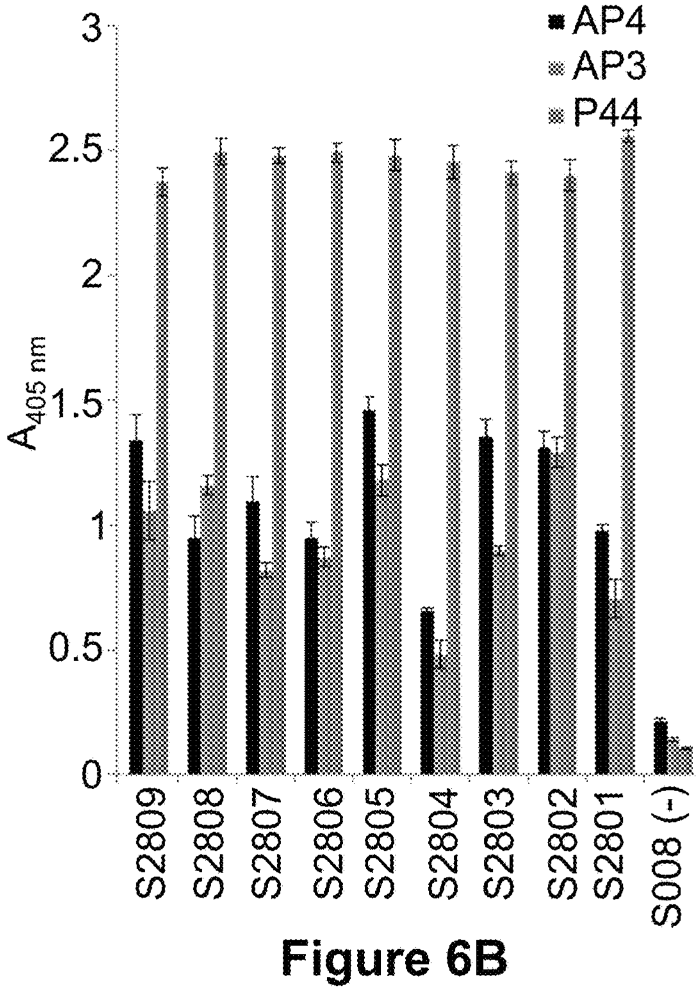

While the AP constructs are designed proteins (not natural proteins), if the epitopes that comprise the chimeritopes are presented on the Aph cell surface by OmpA, Asp14 and AipA, then these epitopes should trigger an antibody response during infection and that antibody should be able to bind to the AP proteins. To test this, recombinant AP3v1 and AP4v1 were immobilized in ELISA plate wells and screened with serum from Aph infected dogs. Note that recombinant P44 protein served as a positive control for antibody binding. P44 has been demonstrated to consistently induce antibody formation in infected mammals. P44 and the AP proteins were bound by antibody present in serum of infected dogs (FIG. 6B). These analyses revealed several important findings. First, the epitopes that were selected for inclusion in the AP constructs are naturally antigenic and are presented on the cell surface. Second, when the epitopes are isolated from their proteins of origin and presented in the context of chimeritopes, they retain the ability to bind to antibody that develops during natural infection. Lastly, from this it can be concluded that antibody elicited by vaccination with the AP chimeritopes will bind to the epitopes of OmpA, Asp14 and AipA as presented on the cell surface of Aph.

Example 3. Generation of Antiserum Against the AP Chimeritopes in Beagle Dogs Using Novel Vaccine Formulations The objective of this study was to generate immune serum in dogs against the AP chimeritopes and determine if the canine hyperimmune sera can block Aph invasion of HL60 cells at levels similar to that observed with the analogous anti-AP antisera generated in rats and rabbits. Chimeritopes (AP1v1 to AP4v1) were formulated in REHYDRAGEL® or QUILA®/Cholesterol/CpG for inoculation of dogs. Twenty-seven female purpose-bred Beagles, ~21 weeks of age at day 0, and seronegative for *E. canis* and *A. phagocytophilum*, were randomly assigned to nine treatment groups (T01-T09; 3 dogs/treatment group). All dogs were vaccinated according to the study design presented in the table below. Blood was collected as indicated with terminal blood samples collected on days 54 or 55.

STUDY DESIGN

| Treatment Group | # of Dogs | Treatment | Day | Dose | Route |
|---|---|---|---|---|---|
| T01 | 3 | AP1v1 + REHYDRAGEL ® | 0, 21, | 1 ml | SC |
| T02 | 3 | AP2v1 + REHYDRAGEL ® | 42 | 1 ml | SC |
| T03 | 3 | AP3v1 + REHYDRAGEL ® | | 1 ml | SC |
| T04 | 3 | AP4v1 + REHYDRAGEL ® | | 1 ml | SC |
| T05 | 3 | AP1v1 + QUIL A ® + Cholesterol/CpG | | 1 ml | SC |
| T06 | 3 | AP2v1 + QUIL A ® + Cholesterol/CpG | | 1 ml | SC |
| T07 | 3 | AP3v1 + QUIL A ® + Cholesterol/CpG | | 1 ml | SC |
| T08 | 3 | AP4v1 + QUIL A ® + Cholesterol/CpG | | 1 ml | SC |
| T09 | 3 | AP1v1 + AP2v1 + AP3v1 + AP4v1 + QUIL A ® + Cholesterol/CpG | | 1 ml | SC |

Each AP chimeritope was formulated at 50 μg/dose in a total volume of 1 ml. The study was conducted according to the protocol with the following exceptions: 1) Injection site observations on day 42 (pre-vaccination) through day 49 (left and right neck) were added. 2) Additional weekly observations were added for reactions at the injection site that continued beyond the seven-day observation period. 3) Half of the dogs were terminated on day 54, and the remaining on day 55.

The following were deviations from the protocol: 1) blood was to be collected on day 0, 21, 35, 42 and 56 of study (2 on days 0, 21, 35, 42 and final large bleed 200 mLs on day 56/dog). 2) Blood was collected on day 36 (not day 35). 3) Body temperatures were determined pre- and post-vaccination on day 0 through 7, 21-28 and 42-49. Body temperatures were also determined at the time an animal was removed from study (day 55 or 56). No adverse events occurred during the duration of this study.

The results of this study demonstrated that AP1, AP2, AP3v1 and AP4v1 induced high IgG titer antibody responses in canines as measured by endpoint dilution ELISA (data not shown). Some dogs were found to have low level titers to some AP proteins prior to vaccination. The origins of this background binding are not clear. Serum samples with high background levels of antibody were excluded from further analysis. As described below, the serum samples were then pooled and used in blocking experiments. In these experiments microscopy was employed to assess infection and the number of Aph vacuoles (ApVs) that form in each infected cell.

Example 4. Assessment of the Ability of Anti-Chimeritope Antisera Alone or in Combination with Anti-APH_1235 and/or P130 Antisera to Inhibit Aph Infection of HL60 Cells To conduct these assays detailed within, cultures of infection free and Aph infected HL60 cells are required. The infected and uninfected HL60 cells were cultivated in Iscove's modified Dulbecco media (10% FBS; 37 C; humified chamber; 5% $CO_2$). To obtain purified Aph cells, infected HL60 cells were sonicated and the bacteria were recovered by differential centrifugation. To conduct the antibody blocking experiments, purified Aph cells were incubated with $2.5\times10^6$ uninfected HL-60 cells in the presence of the desired hyperimmune serum derived animals (rat, rabbit or dogs) vaccinated with individual AP proteins, combinations of AP protein, P130 and APH_1235. The antisera were used at dilutions ranging from 1:5 to 1:625 (as indicated in each experiment). Negative controls consisted of preimmune serum or anti-OspC antiserum. After combining the cells and desired sera, the samples were gently mixed. After the incubation period, the unbound bacteria were removed by washing and the population of infected and uninfected HL60 cells were recovered by centrifugation. The cells were suspended at 250,000 cells per ml and incubated as above. At 24 h, aliquots of 35,000 cells were placed on slides, fixed and permeabilized using ice cold methanol. To perform IFA analyses, the slides were incubated with 5% bovine serum albumin (BSA) in PBS for 1 h; washed, and incubated with rabbit anti-P44 antiserum (1:500 dilution; PBS with 1% BSA; 30 min). The slides were then washed with PBS, incubated with Alexa Fluor-488 conjugated goat anti-rabbit IgG (in PBS with 1% BSA; 30 min), washed, and mounted with PROLONG® Gold Antifade medium containing 4',6-diamidino-2-phenylindole (DAPI). The percentage of cells with at least one ApV was determined by analysis of 100 cells in triplicate. Similarly, the number of ApVs per cell was also determined. To test for significant differences among groups, one-way analysis of variance was determined using Tukey's post hoc test (Prism 5.0; GraphPad; San Diego, CA) and to assess statistical significance among pairs the student's t-test was employed (P values of <0.05 were set).

Figure 7A:
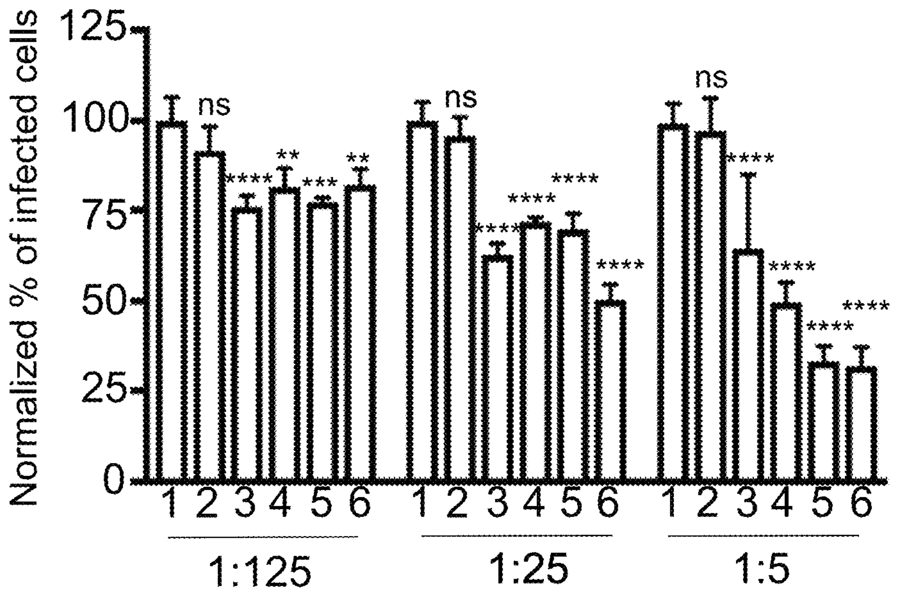
FIGS. 7A and B. Comparative analyses of the ability of antisera against AP1v1, AP2v1, AP3v1 and AP4v1 to inhibit Aph infection of HL60 cells. Sera from dogs vaccinated with AP proteins were incubated at different concentrations (1:125; 1:25 and 1:5 final dilutions) with HL60 cells and Aph cells. The purpose of this experiment was to determine if vaccine induced antibody can block infection and do so in a dose-dependent manner After incubation, the percentage of HL60 cells that became infected (A) and the mean number of Aph vacuoles (ApVs) per cell (B) was determined and the data graphed. Preimmune serum and antisera raised against the *Borrelia* Osp (irrelevant antibody) served as negative controls (Bars 1 and 2, respectively). Bars 3, 4, 5 and 6 show the results obtained with sera raised against AP1v1 (SEQ ID NO: 8), AP2v1 (SEQ ID NO: 10), AP3v1 (SEQ ID NO: 12) and AP4v1(SEQ ID NO: 14) at the dilutions indicated. Significance values relative to preimmune serum are indicated (*P<0.05; P<0.01; *P<0.001; ****P<0.0001; ns=not significant). The data reveal that all APv1 series proteins inhibit to varying degrees the intracellular localization of *Anaplasma*.
Figure 7B:
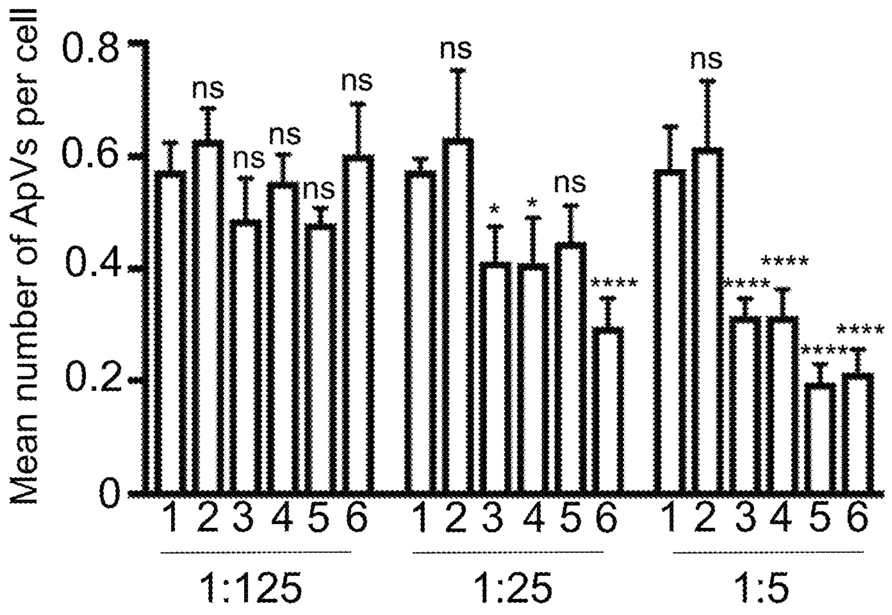

Results:

Rat anti-AP1v1, APv2, AP3v1 and APv2 antisera significantly reduced the percentage of infected cells (FIG. 7A) and the mean number of ApVs per cell (FIG. 7B) in a dose-dependent manner Antisera dilution ranging from 1:5 to 1:125 were tested. The negative control sera (preimmune and anti-OspC antisera) had no effect. Antibody to AP3v1 and AP4v1 displayed the most efficient blocking (see FIGS. 7A and 7B at the 1:5 dilution). Thus, immunization of rats against chimeritopes bearing the binding domain sequences of OmpA, Asp14, and AipA promotes production of antibodies that can significantly reduce the ability of Aph to infect host cells.

Figure 8A:
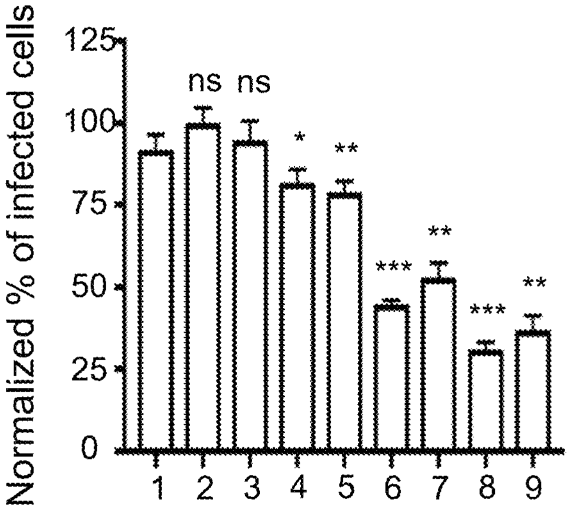
FIGS. 8A and B. Comparative analysis of the inhibition of Aph infection of HL60 cells by canine anti-AP3v1 and canine anti-AP4v1 antisera generated using different adjuvants. The influence of adjuvant on the ability of antibody induced by vaccination with the APv1 series of proteins to block Aph invasion and vacuoles number per cell was assessed. The assays were conducted as detailed in FIGS. 7A and B. (A) indicates the percentage of infected cells and (B) indicates the mean number of Aph vacuoles (ApVs) per cell. In each figure, bar graph designations are as follows: Bar 1—preimmune serum; Bar 2—AP1v1+REHYDRAGEL®; Bar 3—AP1v1+QCT; Bar 4—AP2v1+REHYDRAGEL®; Bar 5—AP2v1+QCT; Bar 6—AP3v1+REHYDRAGEL®; Bar 7—AP3v1+QCT; Bar 8—AP4v1+QCT; Bar 9—AP1v1, AP2v1, AP3v1, AP4v1+QCT. Statistically significant values relative to preimmune serum are indicated (*P<0.05; P<0.01; *P<0.001; ****P<0.0001; ns=not significant).
Figure 8B:
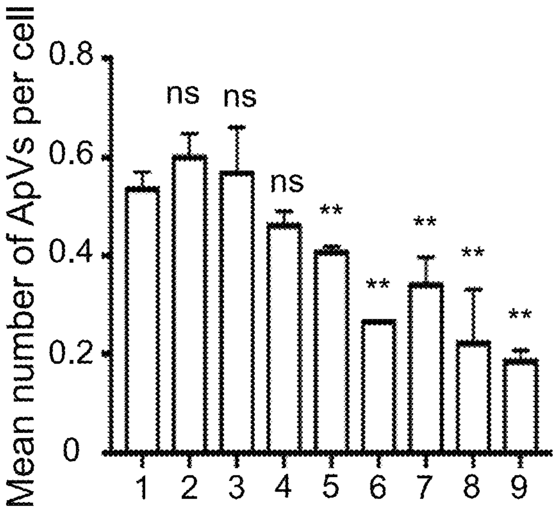

It was next examined if immunization of dogs with AP1v1, AP2v1, AP3v1, AP4v1, or a combination of all four chimeritopes, elicits antibodies that interfere with Aph infectivity (FIG. 8A) or mean numbers of ApVs per cell (FIG. 8B). Antisera were generated using two different adjuvants: REHYDRAGEL® adjuvant or QUILA®/cholesterol/CpG (QCT). After generating the antisera, Aph bacteria were incubated with HL-60 cells for 1 h in the presence of 1:5 dilutions of pooled sera obtained from dogs that had been immunized with each individual chimeritope, or a combination of all four. Preimmune canine serum served as a negative control. Examination at 24 h post-infection revealed that canine antisera against AP1v1, AP2v1, AP3v1, AP4v1, or all four APv1 chimeritopes significantly reduced the percentage of infected cells (FIG. 8A) and lowered the number of ApVs per cell (FIG. 8B). The most effective inhibitory activity was observed with antisera elicited by AP3v1, AP4v1, or all four chimeritopes in combination. These data demonstrate that immunization of dogs with the AP constructs induces production of antibodies capable of inhibiting Aph infection of host cells.

Figure 9A:
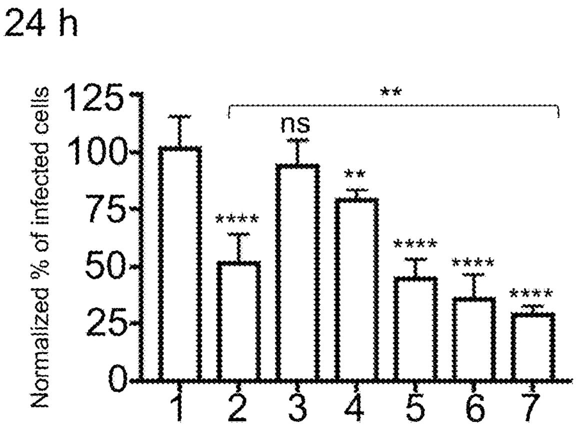
FIG. 9A-D. Antibody to P130 and APH_1235 enhance the blocking ability of rat anti-AP4v1 antiserum. The blocking ability of antibody elicited in rats by vaccination with the antigens listed below was determined after 24 h (A) and (B) or 72 h (C) and (D) post-infection. In (A) and (C) the data are presented as "normalized percentage of infected cells". In (B) and (D), the data are presented as the mean number of Aph vacuoles (ApVs) per 100 cells. In (A)-(D), bar graph designations are as follows: 1) rat preimmune serum; 2) anti-Ap4v1(rat); 3) anti-P130 (rabbit); 4) anti-APH_1235 (rabbit); 5) anti-Ap4v1+anti-P130; 6) anti-Ap4v1+anti-APH_1235; 7) anti-AP4v1+anti-P130+anti-APH_1235. Statistically significant (*P<0.05; P<0.01; *P<0.001; ****P<0.0001) values relative to preimmune serum are indicated; ns=not significant. Brackets designate whether or not the two samples that the brackets demarcate are statistically significantly different from each other.
Figure 9B:
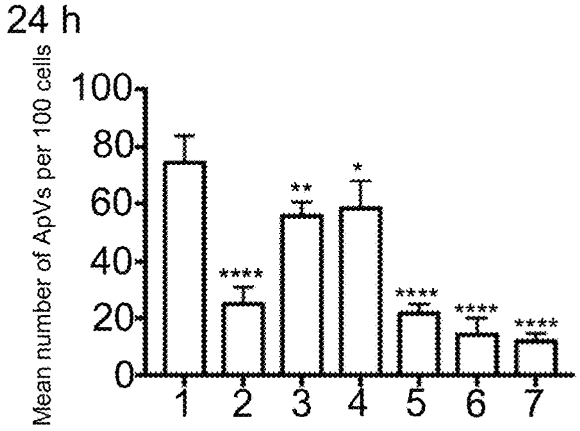
Figure 9C:
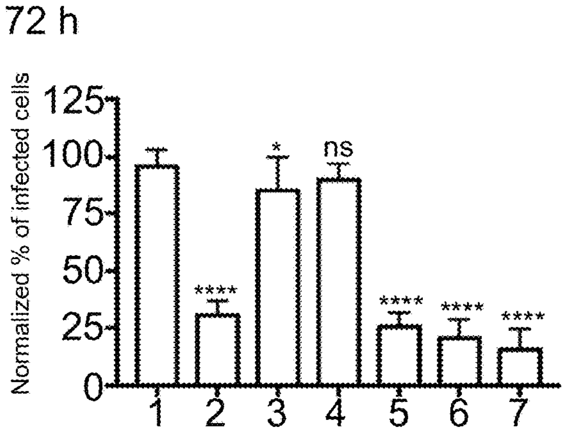
Figure 9D:
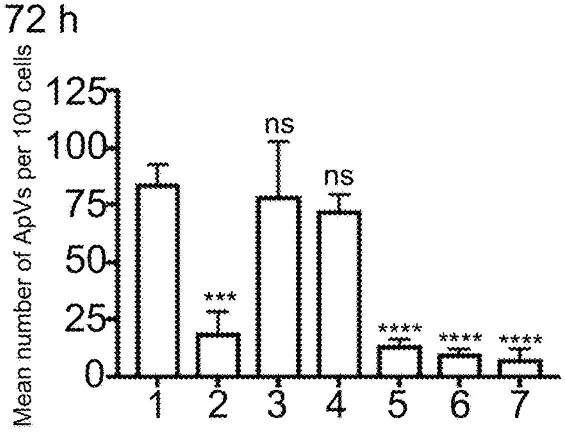
Figure 10A:
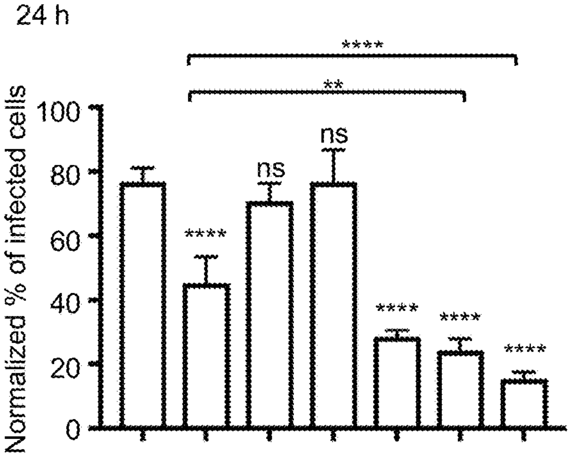
FIG. 10A-D. Antibody to P130 and APH_1235 enhance the blocking ability of canine anti-AP4v1 antiserum. The blocking ability of antibody elicited in dogs by vaccination with the antigens listed below was determined after 24 h (A) and (B) or 72 h (C) and (D) post-infection. In (A) and (C), the data are presented as "normalized percentage of infected cells". In (B) and (D), the data are presented as the mean number of Aph vacuoles (ApVs) per 100 cells. In (A)-(D), bar designations are as follows: 1) canine preimmune serum; 2) anti-Ap4v1(canine); 3) anti-P130 (rabbit); 4) anti-APH_1235 (rabbit); 5) anti-Ap4v1+anti-P130; 6) anti-Ap4v1+anti-APH_1235; 7) anti-AP4v1+anti-P130+anti-APH_1235. Statistically significant (****P<0.0001) values relative to preimmune serum are indicated; ns=not significant. Brackets designate whether or not the two samples that the brackets demarcate are statistically significant from each other.
Figure 10B:
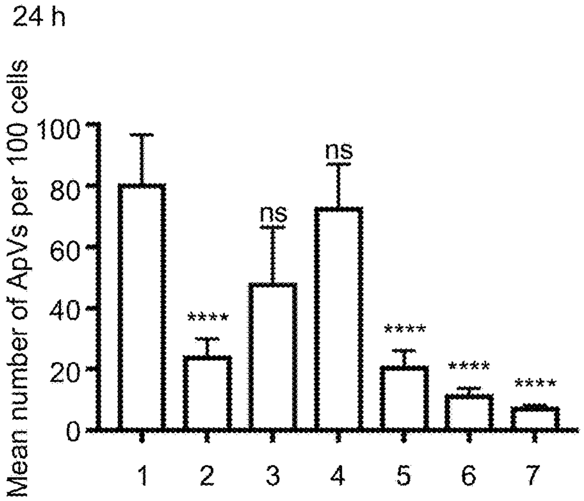
Figure 10C:
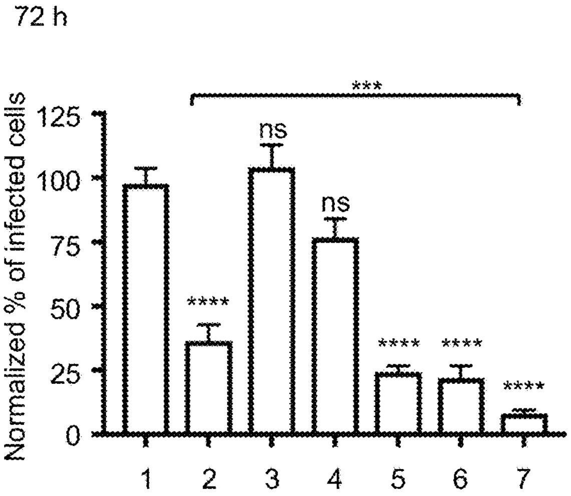
Figure 10D:
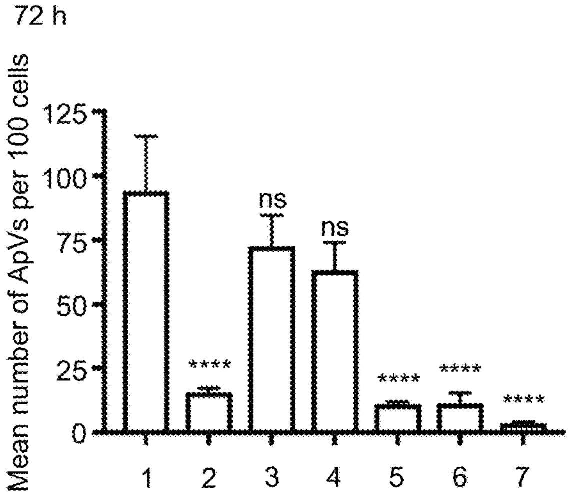

To determine if antisera raised against additional virulence factors of Aph, specifically P130 and APH_1235 could enhance the infection blocking activity of the anti-AP antisera we turned back to the rat model for initial analyses. To test this, we focused on rat anti-AP4v1 antisera. Aph bacteria were incubated with HL-60 cells in the presence of 1:5 dilutions of rat anti-AP4v1 antiserum, rabbit antiP130 antiserum, rabbit anti-APH_1235 antiserum, antisera against AP4v1 and P130, AP4v1 and APH_1235, all three antisera, or preimmune serum (see FIG. 9A and FIG. 9B). The number of infected cells and the mean number of ApVs per 100 cells were determined after 24 and 72 h. The most effective infection-blocking activity was observed for the anti-AP4v1-P130-APH_1235 antisera combination. Therefore, inclusion of antisera specific for APH_1235 and/or P130 augments and enhances the inhibitory activity of AP4v1 antisera against Aph infection of host cells.

In a manner similar to the experiments detailed above that used antisera generated in rats, we next determined if the blocking ability of canine anti-AP4v1 antiserum could also be improved by combining it with anti-P130 and/or anti-APH_1235 antisera (FIG. 10A-D). Note that the anti-APH_1235 and anti-P130 antisera used in this experiment were generated in rabbits. Aph bacteria were incubated with HL-60 cells in the presence of canine anti-AP4v1 antiserum alone, rabbit anti-P130 antiserum alone, rabbit anti-APH_1235 antiserum alone, antisera against AP4v1 and P130, AP4v1 and APH_1235, or all three antisera. The most effective infection blocking capability was observed for the anti-AP4v1-P130-APH_1235 antisera combination. Overall these data confirm that canine anti-AP4v1 antiserum's inhibitory capability against Aph infection is augmented by the addition of anti-APH_1235 and/or anti-P130 antisera.

Figure 11A:
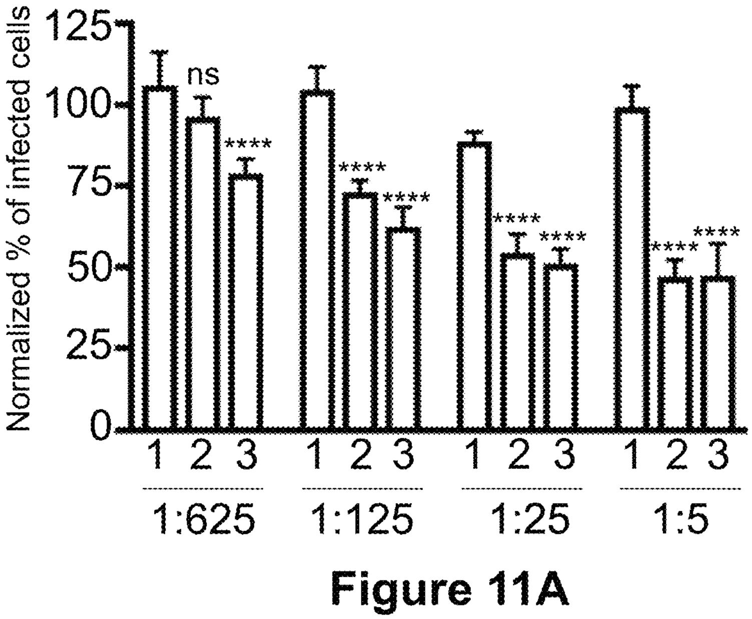
FIGS. 11A and B. In vitro inhibition of Aph infection using rat anti-AP3v2 or anti-AP4v2 antisera. In vitro inhibition of Aph infection by rat anti-AP3v2 (SEQ ID NO: 13) or AP4v2 (SEQ ID NO: 15) antiserum was assessed. Aph organisms were incubated in the presence of rat anti-AP3v2 or rat anti-AP4v2 antisera at varying dilutions. (A) presents the results expressed as normalized % of infected cells and (B) indicates the mean number of Aph vacuoles (ApVs) per 100 cells. In each figure, bar designations are as follows: 1) rat preimmune; 2) rat anti-AP3v2; 3) rat anti-AP4v2. Statistically significant (P<0.01; *P<0.001; ****P<0.0001) values relative to preimmune serum are indicated; ns=not significant.
Figure 11B:
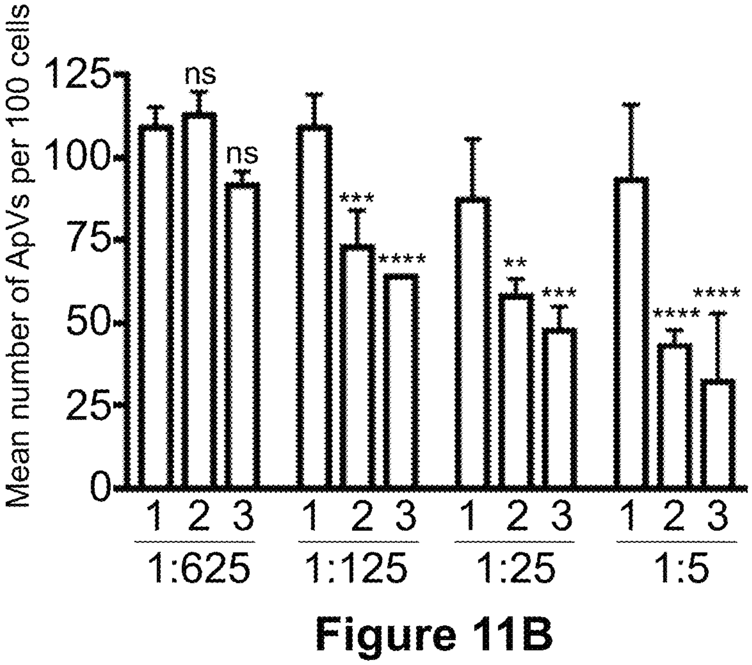

AP1v1, AP2v1, AP3v1, and AP4v1 consist of arrangements of epitopes of the following sequences: Asp14 (LKLERAVYGANTPKES; SEQ ID NO: 4); AipA (SLDPTQGSHTAENI; SEQ ID NO: 3) and OmpA (GKYDLKGPGKKVILELEVQL; SEQ ID NO: 1). In the context of the AP3 and AP4 chimeritopes, a second variant of the OmpA epitope sequence was tested (GKYDLKGPGKKVILELVEQL; SEQ ID NO: 2). The difference between SEQ ID NO:1 and 2 is subtle and consists of a reversal of the two amino acids that are underlined. To determine if this sequence difference might impact blocking ability of the anti-AP antisera, rats were immunized with AP3v2 and AP4v2. The anti-AP3v2 and anti-AP4v2 effectively inhibited Aph infection in a dose-dependent manner at levels similar to that of the anti-AP3v1 and anti-AP4v1 (FIG. 11).

Figure 12A:
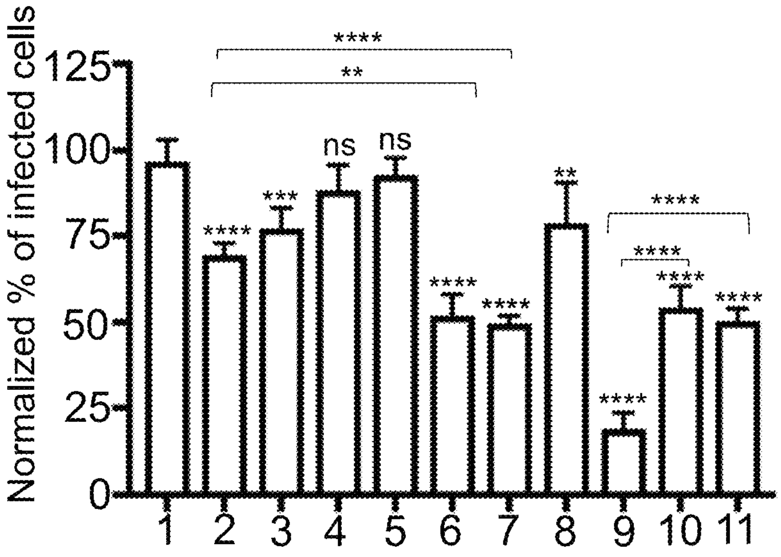
FIGS. 12A and B. Blocking of Aph infection using different combinations of anti-APv4, anti-P130, anti-APH_1235 and anti-P44 antisera. Aph was incubated in the presence of 1:5 dilutions of the sera indicated below. In (A) and (B), the data are presented as the percentage of infected cells and the mean number of ApVs per cell, respectively. In each of (A) and (B), the bar designations are as follows: 1) rat preimmune serum; 2) anti-AP4v2 (rat); 3) anti-APH_1235 (rabbit); 4) anti-P130 (rabbit); 5) anti-P44 (rabbit); 6) anti-AP4v2+anti-APH_1235; 7) anti-AP4v2+P130; 8) anti-AP4v2 AS+anti-P44; 9) anti-AP4v2+anti-APH_1235+anti-P130; 10) anti-AP4v2+anti-APH_1235+anti-P44; 11) anti-AP4v2+anti-P130+anti-P44. Statistically significant (P<0.01; **P<0.0001) values relative to preimmune serum are indicated; ns=not significant. Brackets designate whether or not the two samples that the brackets demarcate are statistically significantly different from each other. The data demonstrate that, in some aspects, an optimal antibody response in terms of both IgG titer and ability to block intracellular invasion is generated by vaccination with AP4v2, P130 and APH-1235 proteins.
Figure 12B:
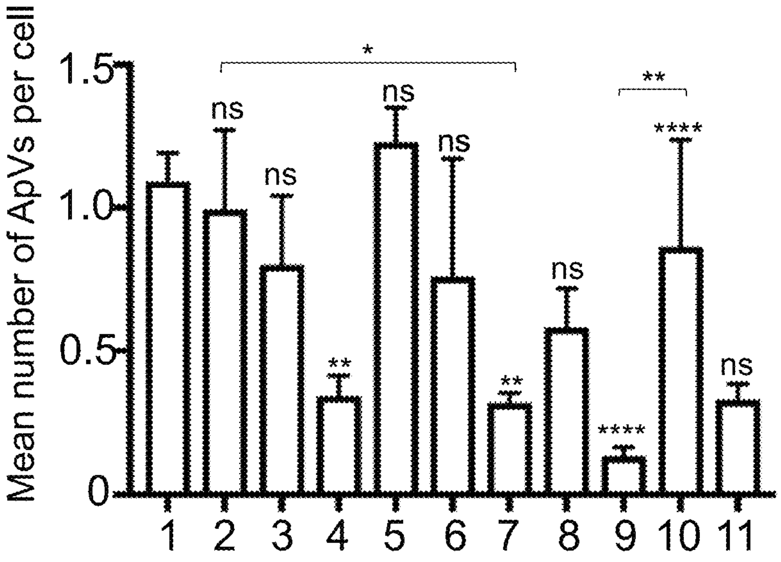

As detailed above, when antisera from rats vaccinated with AP4v1 was combined with anti-P130 and anti-APH_1235 antisera, optimal infection blocking activity was observed. To be complete, we sought to determine if this would also be the case if rat anti-AP4v2 was combined with anti-P130, anti-APH_1235 antisera or combinations thereof. The most effective infection blocking capability was observed for the anti-AP4v2-P130-APH_1235 antisera combination. Note that as an additional control set in this experiment, in some samples the anti-APH_1235 and anti-P130 antisera was replaced with anti-P44 antisera. The purpose of swapping anti-P44 antiserum for anti-APH_1235 or P130 antiserum was to determine if the synergistic blocking observed when anti-AP4v2 antiserum was combined with anti-APH_1235 and anti-P130 antisera was due to antibody specific mediated inhibition resulted simply from the coating of bacteria with antibodies that sterically hinder bacterial access to the host cell surface. The anti-AP4v2-P130-APH_1235 antisera cocktail proved to be significantly more effective at reducing Aph infection and vacuole numbers than antiserum cocktails containing anti-P44 antibody (FIG. 12). Collectively, the data presented above demonstrate that a multi-target, multi-valent approach is required to efficiently inhibit the ability of Aph to invade host cells and establish a productive infection.

Example 5. Evaluation of AP Vaccine Formulations in Beagle Dogs

The objective of this study is to evaluate two different vaccine formulations in dogs. One formulation consists of two different AP chimeritopes (AP3v2 and AP4v2) and the other of the same two chimeritopes in combination with APH_1235 and P130. Both vaccine formulations are adjuvanted with QUIL A®/Cholesterol/CpG.

Thirty-six (36) female purpose-bred Beagles, approximately 21 weeks of age at Day 0, and seronegative for *E. canis* and Aph, are randomly assigned to three treatment groups (T01-T03, 12 dogs/treatment group). All dogs are vaccinated according to the study design on Days 0 and 21. Blood is collected on Days 0, 21, and 42 (prior to vaccinations), and then every 3 days starting at Day 45 through the end of the study.

STUDY DESIGN

| Group | # dogs | Treatment | Vaccination Days | Vaccination Dose | Vaccination Adjuvant | Vaccination Route | Challenge | Blood Collection |
|---|---|---|---|---|---|---|---|---|
| T01 | 12 | Placebo | 0, 21 | 1.0 ml | — | SQ | Day 42 | Days 0, 21, 42, every 3 days starting on Day 45 through the end of the study |
| T02 | 12 | AP3v2 + AP4v2 | | 1.0 ml | QCT* | | | |
| T03 | 12 | AP3v2 + AP4v2 + APH_1235 + P130 | | 1.0 ml | QCT | | | |

*QCT = QuilA ®/Cholesterol/CpG

The primary variable assessed for this study is the presence and the duration of thrombocytopenia post-challenge. Clinical signs monitored/measured include at least fever, lethargy, depression, swollen lymph nodes, and bleeding. The administration of two chimeritopes (AP3v2; AP4v2), and the same two chimeritopes in combination with two other Aph antigens (APH_1235; P130) causes a reduction in at least one measured post challenge clinical variable.

Example 6. Generation of Monoclonal Antibodies Recognizing AP4v2

Four Balb/c mice are immunized with AP4v2 protein at Maine Biotechnology Services (Portland, Me.) according to their optimized, proprietary MBS Rapid Immunization Multiple Sites (RIMMS) protocol. Mice are immunized 4 or 5 times within a 20-day period, at multiple sites on each animal, on each injection date. The primary immunization is prepared 1:1 in Freund's Complete Adjuvant (FCA); subsequent boosts are prepared in Freund's Incomplete Adjuvant (IFA). At day 20, test bleeds are taken and screened by ELISA, to determine the antibody titer. If the titers from any of the mice are sufficiently high, that mouse is selected for fusion. If all the mouse titers are insufficient for fusion, the mice receive an additional boost of antigen (100 μg in IFA). Ten days following the boost, a test bleed is taken and screened by ELISA. This cycle is repeated, if necessary, until at least one mouse is at a sufficient titer warranting fusion. The selected mouse receives an unadjuvanted protein boost (resuspended in saline) four days prior to fusion. Splenocytes removed from the mouse are fused with SP2/0 mouse myeloma cells. Following the fusion, the resulting products are distributed among twenty 96-well plates, and allowed to grow into colonies. Following this, the 96-well plates are doubled-screened in ELISA assays with both a positive screen (AP4v2 protein) and a negative screen (irrelevant 6× His-tagged protein). Colonies that are positive for the AP4v2 protein, but negative for the irrelevant 6× His-tagged protein, are selected for scale-up.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of eliciting an immune response to *Anaplasma* in a subject in need thereof, comprising administering to the subject an amount of a pharmaceutical composition comprising a recombinant, chimeric polypeptide, wherein the amino acid sequence of the recombinant, chimeric polypeptide is selected from the group consisting of:

SEQ ID NO: 8;
SEQ ID NO: 9;
SEQ ID NO: 10;
SEQ ID NO: 11;
SEQ ID NO: 12;
SEQ ID NO: 13;
SEQ ID NO: 14;
SEQ ID NO: 15;
SEQ ID NO: 16;
SEQ ID NO: 17;
SEQ ID NO: 18;
SEQ ID NO: 19;
SEQ ID NO: 20;
SEQ ID NO: 21;
SEQ ID NO: 22;

and

SEQ ID NO: 23, wherein the amount is sufficient to elicit an immune response in the subject.

2. A method of blocking or attenuating the binding of *Anoplasma* to mammalian cells in a subject in need thereof, comprising administering to the subject a pharmaceutical composition comprising a recombinant, chimeric polypeptide, wherein the amino acid sequence of the recombinant, chimeric polypeptide is SEQ ID NO: 13 or

SEQ ID NO: 15, wherein the pharmaceutical composition is administered in an amount sufficient to elicit the production of antibodies that block or attenuate the binding of *Anaplasma* to mammalian cells in the subject.

* * * * *

SEQUENCE LISTING

<160> NUMBER OF SEQ ID NOS: 25

<210> SEQ ID NO 1
<211> LENGTH: 20
<212> TYPE: PRT
<213> ORGANISM: Artificial Sequence
<220> FEATURE:
<223> OTHER INFORMATION: Synthetic invasion domain

<400> SEQUENCE: 1

Gly Lys Tyr Asp Leu Lys Gly Pro Gly Lys Lys Val Ile Leu Glu Leu
1 5 10 15

Glu Val Gln Leu
20

<210> SEQ ID NO 2
<211> LENGTH: 20
<212> TYPE: PRT
<213> ORGANISM: Artificial Sequence
<220> FEATURE:
<223> OTHER INFORMATION: Synthetic invasion domain

<400> SEQUENCE: 2

Gly Lys Tyr Asp Leu Lys Gly Pro Gly Lys Lys Val Ile Leu Glu Leu
1 5 10 15

Val Glu Gln Leu
20

<210> SEQ ID NO 3
<211> LENGTH: 14
<212> TYPE: PRT
<213> ORGANISM: Artificial Sequence
<220> FEATURE:
<223> OTHER INFORMATION: Synthetic invasion domain

<400> SEQUENCE: 3

Ser Leu Asp Pro Thr Gln Gly Ser His Thr Ala Glu Asn Ile
1 5 10

<210> SEQ ID NO 4
<211> LENGTH: 16
<212> TYPE: PRT
<213> ORGANISM: Artificial Sequence
<220> FEATURE:
<223> OTHER INFORMATION: Synthetic invasion domain

<400> SEQUENCE: 4

Leu Lys Leu Glu Arg Ala Val Tyr Gly Ala Asn Thr Pro Lys Glu Ser
1 5 10 15

<210> SEQ ID NO 5
<211> LENGTH: 10
<212> TYPE: PRT
<213> ORGANISM: Artificial Sequence
<220> FEATURE:
<223> OTHER INFORMATION: Synthetic cap sequence

<400> SEQUENCE: 5

Pro Val Val Ala Glu Ser Pro Lys Lys Pro
1 5 10

<210> SEQ ID NO 6
<211> LENGTH: 10
<212> TYPE: PRT
<213> ORGANISM: Artificial Sequence
<220> FEATURE:

-continued

```
<223> OTHER INFORMATION: Synthetic cap sequence

<400> SEQUENCE: 6

Pro Val Val Pro Pro Ser Pro Lys Lys Pro
1               5                   10


<210> SEQ ID NO 7
<211> LENGTH: 10
<212> TYPE: PRT
<213> ORGANISM: Artificial Sequence
<220> FEATURE:
<223> OTHER INFORMATION: Synthetic cap sequence

<400> SEQUENCE: 7

Pro Val Val Pro Pro Ser Pro Pro Lys Pro
1               5                   10


<210> SEQ ID NO 8
<211> LENGTH: 166
<212> TYPE: PRT
<213> ORGANISM: Artificial Sequence
<220> FEATURE:
<223> OTHER INFORMATION: Syntheic chimeritope

<400> SEQUENCE: 8

Gly Lys Tyr Asp Leu Trp Gly Lys Tyr Asp Leu Lys Gly Pro Gly Lys
1               5                   10                  15

Lys Val Ile Leu Glu Leu Glu Val Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Leu Lys Leu Glu Arg Ala Val Tyr
    50                  55                  60

Gly Ala Asn Thr Pro Lys Glu Ser Ser Leu Asp Pro Thr Gln Gly Ser
65                  70                  75                  80

His Thr Ala Glu Asn Ile Gly Lys Tyr Asp Leu Lys Gly Pro Gly Lys
                85                  90                  95

Lys Val Ile Leu Glu Leu Glu Val Gln Leu Ser Leu Asp Pro Thr Gln
            100                 105                 110

Gly Ser His Thr Ala Glu Asn Ile Gly Lys Tyr Asp Leu Lys Gly Pro
        115                 120                 125

Gly Lys Lys Val Ile Leu Glu Leu Glu Val Gln Leu Leu Lys Leu Glu
    130                 135                 140

Arg Ala Val Tyr Gly Ala Asn Thr Pro Lys Glu Ser Pro Val Val Ala
145                 150                 155                 160

Glu Ser Pro Lys Lys Pro
                165


<210> SEQ ID NO 9
<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 9

Gly Lys Tyr Asp Leu Trp Gly Lys Tyr Asp Leu Lys Gly Pro Gly Lys
1               5                   10                  15

Lys Val Ile Leu Glu Leu Val Glu Gln Leu Ser Leu Asp Pro Thr Gln
            20                  25                  30
```

-continued

Gly Ser His Thr Ala Glu Asn Ile Leu Lys Leu Glu Arg Ala Val Tyr
35 40 45

Gly Ala Asn Thr Pro Lys Glu Ser Leu Lys Leu Glu Arg Ala Val Tyr
50 55 60

Gly Ala Asn Thr Pro Lys Glu Ser Ser Leu Asp Pro Thr Gln Gly Ser
65 70 75 80

His Thr Ala Glu Asn Ile Gly Lys Tyr Asp Leu Lys Gly Pro Gly Lys
85 90 95

Lys Val Ile Leu Glu Leu Val Glu Gln Leu Ser Leu Asp Pro Thr Gln
100 105 110

Gly Ser His Thr Ala Glu Asn Ile Gly Lys Tyr Asp Leu Lys Gly Pro
115 120 125

Gly Lys Lys Val Ile Leu Glu Leu Val Glu Gln Leu Leu Lys Leu Glu
130 135 140

Arg Ala Val Tyr Gly Ala Asn Thr Pro Lys Glu Ser Pro Val Val Ala
145 150 155 160

Glu Ser Pro Lys Lys Pro
165

<210> SEQ ID NO 10
<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 10

Leu Lys Leu Glu Arg Trp Leu Lys Leu Glu Arg Ala Val Tyr Gly Ala
1 5 10 15

Asn Thr Pro Lys Glu Ser Gly Lys Tyr Asp Leu Lys Gly Pro Gly Lys
20 25 30

Lys Val Ile Leu Glu Leu Glu Val Gln Leu Ser Leu Asp Pro Thr Gln
35 40 45

Gly Ser His Thr Ala Glu Asn Ile Gly Lys Tyr Asp Leu Lys Gly Pro
50 55 60

Gly Lys Lys Val Ile Leu Glu Leu Glu Val Gln Leu Ser Leu Asp Pro
65 70 75 80

Thr Gln Gly Ser His Thr Ala Glu Asn Ile Leu Lys Leu Glu Arg Ala
85 90 95

Val Tyr Gly Ala Asn Thr Pro Lys Glu Ser Leu Lys Leu Glu Arg Ala
100 105 110

Val Tyr Gly Ala Asn Thr Pro Lys Glu Ser Ser Leu Asp Pro Thr Gln
115 120 125

Gly Ser His Thr Ala Glu Asn Ile Gly Lys Tyr Asp Leu Lys Gly Pro
130 135 140

Gly Lys Lys Val Ile Leu Glu Leu Glu Val Gln Leu Pro Val Val Ala
145 150 155 160

Glu Ser Pro Lys Lys Pro
165

<210> SEQ ID NO 11
<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 11

-continued

Leu Lys Leu Glu Arg Trp Leu Lys Leu Glu Arg Ala Val Tyr Gly Ala
1               5                   10                  15

Asn Thr Pro Lys Glu Ser Gly Lys Tyr Asp Leu Lys Gly Pro Gly Lys
            20                  25                  30

Lys Val Ile Leu Glu Leu Val Glu Gln Leu Ser Leu Asp Pro Thr Gln
        35                  40                  45

Gly Ser His Thr Ala Glu Asn Ile Gly Lys Tyr Asp Leu Lys Gly Pro
    50                  55                  60

Gly Lys Lys Val Ile Leu Glu Leu Val Glu Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Leu Lys Leu Glu Arg Ala
            100                 105                 110

Val Tyr Gly Ala Asn Thr Pro Lys Glu Ser Ser Leu Asp Pro Thr Gln
        115                 120                 125

Gly Ser His Thr Ala Glu Asn Ile Gly Lys Tyr Asp Leu Lys Gly Pro
    130                 135                 140

Gly Lys Lys Val Ile Leu Glu Leu Val Glu Gln Leu Pro Val Val Ala
145                 150                 155                 160

Glu Ser Pro Lys Lys Pro
                165

<210> SEQ ID NO 12
<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 12

Gly Lys Tyr Asp Leu Trp Gly Lys Tyr Asp Leu Lys Gly Pro Gly Lys
1               5                   10                  15

Lys Val Ile Leu Glu Leu Glu Val Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Gly Lys Tyr Asp Leu Lys Gly Pro
    50                  55                  60

Gly Lys Lys Val Ile Leu Glu Leu Glu Val Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Gly Lys Tyr Asp Leu Lys
            100                 105                 110

Gly Pro Gly Lys Lys Val Ile Leu Glu Leu Glu Val Gln Leu Ser Leu
        115                 120                 125

Asp Pro Thr Gln Gly Ser His Thr Ala Glu Asn Ile Leu Lys Leu Glu
    130                 135                 140

Arg Ala Val Tyr Gly Ala Asn Thr Pro Lys Glu Ser Pro Val Val Ala
145                 150                 155                 160

Glu Ser Pro Lys Lys Pro
                165

<210> SEQ ID NO 13

-continued

<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 13

```
Gly Lys Tyr Asp Leu Trp Gly Lys Tyr Asp Leu Lys Gly Pro Gly Lys
1               5                   10                  15

Lys Val Ile Leu Glu Leu Val Glu Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Gly Lys Tyr Asp Leu Lys Gly Pro
    50                  55                  60

Gly Lys Lys Val Ile Leu Glu Leu Val Glu Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Gly Lys Tyr Asp Leu Lys
            100                 105                 110

Gly Pro Gly Lys Lys Val Ile Leu Glu Leu Val Glu Gln Leu Ser Leu
        115                 120                 125

Asp Pro Thr Gln Gly Ser His Thr Ala Glu Asn Ile Leu Lys Leu Glu
    130                 135                 140

Arg Ala Val Tyr Gly Ala Asn Thr Pro Lys Glu Ser Pro Val Val Ala
145                 150                 155                 160

Glu Ser Pro Lys Lys Pro
                165
```

<210> SEQ ID NO 14
<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 14

```
Gly Lys Tyr Asp Leu Trp Gly Lys Tyr Asp Leu Lys Gly Pro Gly Lys
1               5                   10                  15

Lys Val Ile Leu Glu Leu Glu Val Gln Leu Gly Lys Tyr Asp Leu Lys
            20                  25                  30

Gly Pro Gly Lys Lys Val Ile Leu Glu Leu Glu Val Gln Leu Gly Lys
        35                  40                  45

Tyr Asp Leu Lys Gly Pro Gly Lys Lys Val Ile Leu Glu Leu Glu Val
    50                  55                  60

Gln Leu Ser Leu Asp Pro Thr Gln Gly Ser His Thr Ala Glu Asn Ile
65                  70                  75                  80

Ser Leu Asp Pro Thr Gln Gly Ser His Thr Ala Glu Asn Ile Ser Leu
                85                  90                  95

Asp Pro Thr Gln Gly Ser His Thr Ala Glu Asn Ile Leu Lys Leu Glu
            100                 105                 110

Arg Ala Val Tyr Gly Ala Asn Thr Pro Lys Glu Ser Leu Lys Leu Glu
        115                 120                 125

Arg Ala Val Tyr Gly Ala Asn Thr Pro Lys Glu Ser Leu Lys Leu Glu
    130                 135                 140

Arg Ala Val Tyr Gly Ala Asn Thr Pro Lys Glu Ser Pro Val Val Ala
```

```
145                 150                 155                 160

Glu Ser Pro Lys Lys Pro
                165


<210> SEQ ID NO 15
<211> LENGTH: 166
<212> TYPE: PRT
<213> ORGANISM: Artificial Sequence
<220> FEATURE:
<223> OTHER INFORMATION: Synthetic chimeritope

<400> SEQUENCE: 15

Gly Lys Tyr Asp Leu Trp Gly Lys Tyr Asp Leu Lys Gly Pro Gly Lys
1               5                   10                  15

Lys Val Ile Leu Glu Leu Val Glu Gln Leu Gly Lys Tyr Asp Leu Lys
            20                  25                  30

Gly Pro Gly Lys Lys Val Ile Leu Glu Leu Val Glu Gln Leu Gly Lys
        35                  40                  45

Tyr Asp Leu Lys Gly Pro Gly Lys Lys Val Ile Leu Glu Leu Val Glu
    50                  55                  60

Gln Leu Ser Leu Asp Pro Thr Gln Gly Ser His Thr Ala Glu Asn Ile
65                  70                  75                  80

Ser Leu Asp Pro Thr Gln Gly Ser His Thr Ala Glu Asn Ile Ser Leu
                85                  90                  95

Asp Pro Thr Gln Gly Ser His Thr Ala Glu Asn Ile Leu Lys Leu Glu
            100                 105                 110

Arg Ala Val Tyr Gly Ala Asn Thr Pro Lys Glu Ser Leu Lys Leu Glu
        115                 120                 125

Arg Ala Val Tyr Gly Ala Asn Thr Pro Lys Glu Ser Leu Lys Leu Glu
    130                 135                 140

Arg Ala Val Tyr Gly Ala Asn Thr Pro Lys Glu Ser Pro Val Val Ala
145                 150                 155                 160

Glu Ser Pro Lys Lys Pro
                165


<210> SEQ ID NO 16
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 16

Gly Lys Tyr Asp Leu Trp Gly Lys Tyr Asp Leu Lys Gly Pro Gly Lys
1               5                   10                  15

Lys Val Ile Leu Glu Leu Glu Val Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Leu Lys Leu Glu Arg Ala Val Tyr
    50                  55                  60

Gly Ala Asn Thr Pro Lys Glu Ser Ser Leu Asp Pro Thr Gln Gly Ser
65                  70                  75                  80

His Thr Ala Glu Asn Ile Gly Lys Tyr Asp Leu Lys Gly Pro Gly Lys
                85                  90                  95

Lys Val Ile Leu Glu Leu Glu Val Gln Leu Ser Leu Asp Pro Thr Gln
            100                 105                 110
```

-continued

```
Gly Ser His Thr Ala Glu Asn Ile Gly Lys Tyr Asp Leu Lys Gly Pro
        115                 120                 125

Gly Lys Lys Val Ile Leu Glu Leu Glu Val Gln Leu Leu Lys Leu Glu
    130                 135                 140

Arg Ala Val Tyr Gly Ala Asn Thr Pro Lys Glu Ser
145                 150                 155


<210> SEQ ID NO 17
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 17

Gly Lys Tyr Asp Leu Trp Gly Lys Tyr Asp Leu Lys Gly Pro Gly Lys
1               5                   10                  15

Lys Val Ile Leu Glu Leu Val Glu Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Leu Lys Leu Glu Arg Ala Val Tyr
    50                  55                  60

Gly Ala Asn Thr Pro Lys Glu Ser Ser Leu Asp Pro Thr Gln Gly Ser
65                  70                  75                  80

His Thr Ala Glu Asn Ile Gly Lys Tyr Asp Leu Lys Gly Pro Gly Lys
                85                  90                  95

Lys Val Ile Leu Glu Leu Val Glu Gln Leu Ser Leu Asp Pro Thr Gln
            100                 105                 110

Gly Ser His Thr Ala Glu Asn Ile Gly Lys Tyr Asp Leu Lys Gly Pro
        115                 120                 125

Gly Lys Lys Val Ile Leu Glu Leu Val Glu Gln Leu Leu Lys Leu Glu
    130                 135                 140

Arg Ala Val Tyr Gly Ala Asn Thr Pro Lys Glu Ser
145                 150                 155


<210> SEQ ID NO 18
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 18

Leu Lys Leu Glu Arg Trp Leu Lys Leu Glu Arg Ala Val Tyr Gly Ala
1               5                   10                  15

Asn Thr Pro Lys Glu Ser Gly Lys Tyr Asp Leu Lys Gly Pro Gly Lys
            20                  25                  30

Lys Val Ile Leu Glu Leu Glu Val Gln Leu Ser Leu Asp Pro Thr Gln
        35                  40                  45

Gly Ser His Thr Ala Glu Asn Ile Gly Lys Tyr Asp Leu Lys Gly Pro
    50                  55                  60

Gly Lys Lys Val Ile Leu Glu Leu Glu Val Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Leu Lys Leu Glu Arg Ala
            100                 105                 110
```

```
Val Tyr Gly Ala Asn Thr Pro Lys Glu Ser Ser Leu Asp Pro Thr Gln
        115                 120                 125

Gly Ser His Thr Ala Glu Asn Ile Gly Lys Tyr Asp Leu Lys Gly Pro
    130                 135                 140

Gly Lys Lys Val Ile Leu Glu Leu Glu Val Gln Leu
145                 150                 155


<210> SEQ ID NO 19
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 19

Leu Lys Leu Glu Arg Trp Leu Lys Leu Glu Arg Ala Val Tyr Gly Ala
1               5                   10                  15

Asn Thr Pro Lys Glu Ser Gly Lys Tyr Asp Leu Lys Gly Pro Gly Lys
            20                  25                  30

Lys Val Ile Leu Glu Leu Val Glu Gln Leu Ser Leu Asp Pro Thr Gln
        35                  40                  45

Gly Ser His Thr Ala Glu Asn Ile Gly Lys Tyr Asp Leu Lys Gly Pro
    50                  55                  60

Gly Lys Lys Val Ile Leu Glu Leu Val Glu Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Leu Lys Leu Glu Arg Ala
            100                 105                 110

Val Tyr Gly Ala Asn Thr Pro Lys Glu Ser Ser Leu Asp Pro Thr Gln
        115                 120                 125

Gly Ser His Thr Ala Glu Asn Ile Gly Lys Tyr Asp Leu Lys Gly Pro
    130                 135                 140

Gly Lys Lys Val Ile Leu Glu Leu Val Glu Gln Leu
145                 150                 155


<210> SEQ ID NO 20
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 20

Gly Lys Tyr Asp Leu Trp Gly Lys Tyr Asp Leu Lys Gly Pro Gly Lys
1               5                   10                  15

Lys Val Ile Leu Glu Leu Glu Val Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Gly Lys Tyr Asp Leu Lys Gly Pro
    50                  55                  60

Gly Lys Lys Val Ile Leu Glu Leu Glu Val Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Gly Lys Tyr Asp Leu Lys
```

-continued

```
            100                 105                 110

Gly Pro Gly Lys Lys Val Ile Leu Glu Leu Glu Val Gln Leu Ser Leu
        115                 120                 125

Asp Pro Thr Gln Gly Ser His Thr Ala Glu Asn Ile Leu Lys Leu Glu
    130                 135                 140

Arg Ala Val Tyr Gly Ala Asn Thr Pro Lys Glu Ser
145                 150                 155


<210> SEQ ID NO 21
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 21

Gly Lys Tyr Asp Leu Trp Gly Lys Tyr Asp Leu Lys Gly Pro Gly Lys
1               5                   10                  15

Lys Val Ile Leu Glu Leu Val Glu Gln Leu Ser Leu Asp Pro Thr Gln
            20                  25                  30

Gly Ser His Thr Ala Glu Asn Ile Leu Lys Leu Glu Arg Ala Val Tyr
        35                  40                  45

Gly Ala Asn Thr Pro Lys Glu Ser Gly Lys Tyr Asp Leu Lys Gly Pro
    50                  55                  60

Gly Lys Lys Val Ile Leu Glu Leu Val Glu Gln Leu Ser Leu Asp Pro
65                  70                  75                  80

Thr Gln Gly Ser His Thr Ala Glu Asn Ile Leu Lys Leu Glu Arg Ala
                85                  90                  95

Val Tyr Gly Ala Asn Thr Pro Lys Glu Ser Gly Lys Tyr Asp Leu Lys
            100                 105                 110

Gly Pro Gly Lys Lys Val Ile Leu Glu Leu Val Glu Gln Leu Ser Leu
        115                 120                 125

Asp Pro Thr Gln Gly Ser His Thr Ala Glu Asn Ile Leu Lys Leu Glu
    130                 135                 140

Arg Ala Val Tyr Gly Ala Asn Thr Pro Lys Glu Ser
145                 150                 155


<210> SEQ ID NO 22
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 22

Gly Lys Tyr Asp Leu Trp Gly Lys Tyr Asp Leu Lys Gly Pro Gly Lys
1               5                   10                  15

Lys Val Ile Leu Glu Leu Glu Val Gln Leu Gly Lys Tyr Asp Leu Lys
            20                  25                  30

Gly Pro Gly Lys Lys Val Ile Leu Glu Leu Glu Val Gln Leu Gly Lys
        35                  40                  45

Tyr Asp Leu Lys Gly Pro Gly Lys Lys Val Ile Leu Glu Leu Glu Val
    50                  55                  60

Gln Leu Ser Leu Asp Pro Thr Gln Gly Ser His Thr Ala Glu Asn Ile
65                  70                  75                  80

Ser Leu Asp Pro Thr Gln Gly Ser His Thr Ala Glu Asn Ile Ser Leu
                85                  90                  95
```

```
Asp Pro Thr Gln Gly Ser His Thr Ala Glu Asn Ile Leu Lys Leu Glu
            100                 105                 110

Arg Ala Val Tyr Gly Ala Asn Thr Pro Lys Glu Ser Leu Lys Leu Glu
        115                 120                 125

Arg Ala Val Tyr Gly Ala Asn Thr Pro Lys Glu Ser Leu Lys Leu Glu
    130                 135                 140

Arg Ala Val Tyr Gly Ala Asn Thr Pro Lys Glu Ser
145                 150                 155


<210> SEQ ID NO 23
<211> LENGTH: 156
<212> TYPE: PRT
<213> ORGANISM: Artificial Sequence
<220> FEATURE:
<223> OTHER INFORMATION: Synthetic chimeritope

<400> SEQUENCE: 23

Gly Lys Tyr Asp Leu Trp Gly Lys Tyr Asp Leu Lys Gly Pro Gly Lys
1               5                   10                  15

Lys Val Ile Leu Glu Leu Val Glu Gln Leu Gly Lys Tyr Asp Leu Lys
            20                  25                  30

Gly Pro Gly Lys Lys Val Ile Leu Glu Leu Val Glu Gln Leu Gly Lys
        35                  40                  45

Tyr Asp Leu Lys Gly Pro Gly Lys Lys Val Ile Leu Glu Leu Val Glu
    50                  55                  60

Gln Leu Ser Leu Asp Pro Thr Gln Gly Ser His Thr Ala Glu Asn Ile
65                  70                  75                  80

Ser Leu Asp Pro Thr Gln Gly Ser His Thr Ala Glu Asn Ile Ser Leu
                85                  90                  95

Asp Pro Thr Gln Gly Ser His Thr Ala Glu Asn Ile Leu Lys Leu Glu
            100                 105                 110

Arg Ala Val Tyr Gly Ala Asn Thr Pro Lys Glu Ser Leu Lys Leu Glu
        115                 120                 125

Arg Ala Val Tyr Gly Ala Asn Thr Pro Lys Glu Ser Leu Lys Leu Glu
    130                 135                 140

Arg Ala Val Tyr Gly Ala Asn Thr Pro Lys Glu Ser
145                 150                 155


<210> SEQ ID NO 24
<211> LENGTH: 619
<212> TYPE: PRT
<213> ORGANISM: Anaplasma phagocytophilum

<400> SEQUENCE: 24

Met Phe Glu His Asn Ile Pro Asp Thr Tyr Thr Gly Thr Thr Ala Glu
1               5                   10                  15

Gly Ser Pro Gly Leu Ala Gly Gly Asp Phe Ser Leu Ser Ser Ile Asp
            20                  25                  30

Phe Thr Arg Asp Phe Thr Ile Glu Ser His Arg Gly Ser Ser Ala Asp
        35                  40                  45

Asp Pro Gly Tyr Ile Ser Phe Arg Asp Gln Asp Gly Asn Val Met Ser
    50                  55                  60

Arg Phe Leu Asp Val Tyr Val Ala Asn Phe Ser Leu Arg Cys Lys His
65                  70                  75                  80

Ser Pro Tyr Asn Asn Asp Arg Met Glu Thr Ala Ala Phe Ser Leu Thr
                85                  90                  95

Pro Asp Ile Ile Glu Pro Ser Ala Leu Leu Gln Glu Ser His Ser Thr
```

-continued

```
            100                 105                 110

Gln Asn Asn Val Glu Glu Ala Val Gln Val Thr Ala Leu Glu Cys Pro
        115                 120                 125

Pro Cys Asn Pro Val Pro Ala Glu Glu Val Ala Pro Gln Pro Ser Phe
    130                 135                 140

Leu Ser Arg Ile Ile Gln Ala Phe Leu Trp Leu Phe Thr Pro Ser Ser
145                 150                 155                 160

Thr Thr Asp Thr Ala Glu Asp Ser Lys Cys Asn Ser Ser Asp Thr Ser
                165                 170                 175

Lys Cys Thr Ser Ala Ser Ser Glu Ser Leu Glu Gln Gln Gln Glu Ser
            180                 185                 190

Val Glu Val Gln Pro Ser Val Leu Met Ser Thr Ala Pro Ile Ala Thr
        195                 200                 205

Glu Pro Gln Asn Ala Val Val Asn Gln Val Asn Thr Thr Ala Val Gln
    210                 215                 220

Val Glu Ser Ser Ile Ile Val Pro Glu Ser Gln His Thr Asp Val Thr
225                 230                 235                 240

Val Leu Glu Asp Thr Thr Glu Thr Ile Thr Val Asp Gly Glu Tyr Gly
                245                 250                 255

His Phe Ser Asp Ile Ala Ser Gly Glu His Asn Asn Asp Leu Pro Ala
            260                 265                 270

Met Leu Leu Asp Glu Ala Asp Phe Thr Met Leu Leu Ala Asn Glu Glu
        275                 280                 285

Ser Lys Thr Leu Glu Ser Met Pro Ser Asp Ser Leu Glu Asp Asn Val
    290                 295                 300

Gln Glu Leu Gly Thr Leu Pro Leu Gln Glu Gly Glu Thr Val Ser Glu
305                 310                 315                 320

Gly Asn Thr Arg Glu Ser Leu Pro Thr Asp Val Ser Gln Asp Ser Val
                325                 330                 335

Gly Val Ser Thr Asp Leu Glu Ala His Ser Gln Glu Val Glu Thr Val
            340                 345                 350

Ser Glu Val Ser Thr Gln Asp Ser Leu Ser Thr Asn Ile Ser Gln Asp
        355                 360                 365

Ser Val Gly Val Ser Thr Asp Leu Glu Ala His Ser Lys Gly Val Glu
    370                 375                 380

Ile Val Ser Glu Gly Gly Thr Gln Asp Ser Leu Ser Ala Asp Phe Pro
385                 390                 395                 400

Ile Asn Thr Val Glu Ser Glu Ser Thr Asp Leu Glu Ala His Ser Gln
                405                 410                 415

Glu Val Glu Thr Val Ser Glu Phe Thr Gln Asp Ser Leu Ser Thr Asn
            420                 425                 430

Ile Ser Gln Asp Ser Val Gly Val Ser Thr Asp Leu Glu Val His Ser
        435                 440                 445

Gln Glu Val Glu Ile Val Ser Glu Gly Gly Thr Gln Asp Ser Leu Ser
    450                 455                 460

Thr Asn Ile Ser Gln Asp Ser Val Gly Val Ser Thr Asp Leu Glu Ala
465                 470                 475                 480

His Ser Gln Glu Val Glu Thr Val Ser Glu Phe Thr Gln Asp Ser Leu
                485                 490                 495

Ser Thr Asn Ile Ser Gln Asp Ser Val Gly Val Ser Thr Asp Leu Glu
            500                 505                 510

Val His Ser Gln Glu Val Glu Ile Val Ser Glu Gly Gly Thr Gln Asp
        515                 520                 525
```

-continued

```
Ser Leu Ser Thr Asn Ile Ser Gln Asp Ser Val Gly Val Ser Thr Asp
    530                 535                 540

Leu Glu Ala His Ser Lys Gly Val Glu Ile Val Ser Glu Gly Gly Thr
545                 550                 555                 560

Gln Asp Ser Leu Ser Ala Asp Phe Pro Ile Asn Thr Val Glu Ser Glu
                565                 570                 575

Ser Thr Asp Leu Glu Ala His Ser Pro Glu Gly Glu Ile Val Ser Glu
            580                 585                 590

Val Ser Thr Gln Asp Ala Pro Ser Thr Gly Val Glu Ile Arg Phe Met
        595                 600                 605

Asp Arg Asp Ser Asp Asp Asp Val Leu Ala Leu
    610                 615


<210> SEQ ID NO 25
<211> LENGTH: 134
<212> TYPE: PRT
<213> ORGANISM: Anaplasma phagocytophilum

<400> SEQUENCE: 25

Met Lys Gly Lys Ser Asp Ser Glu Ile Arg Thr Ser Ser Ser Ile Arg
1               5                   10                  15

Thr Ser Ser Ser Asp Asp Ser Arg Ser Ser Asp Asp Ser Thr Arg Ile
            20                  25                  30

Arg Ala Ser Lys Thr His Pro Gln Ala Pro Ser Asp Asn Ser Ser Ile
        35                  40                  45

Leu Ser Ser Glu Asp Ile Glu Ser Val Met Arg Cys Leu Glu Glu Glu
    50                  55                  60

Tyr Gly Gln Lys Leu Ser Ser Glu Leu Lys Lys Ser Met Arg Glu Glu
65                  70                  75                  80

Ile Ser Thr Ala Val Pro Glu Leu Thr Arg Ala Leu Ile Pro Leu Leu
                85                  90                  95

Ala Ser Ala Ser Asp Ser Asp Ser Ser Ser Arg Lys Leu Gln Glu Glu
            100                 105                 110

Trp Val Lys Thr Phe Met Ala Ile Met Leu Pro His Met Gln Lys Ile
        115                 120                 125

Val Ala Ser Thr Gln Gly
    130
```